(12) United States Patent
Olson

(10) Patent No.: US 6,372,957 B1
(45) Date of Patent: Apr. 16, 2002

(54) TRANSGENIC MOUSE COMPRISING A MEF2 BINDING SITE OPERATIVELY LINKED TO AN INDICATOR GENE AND METHODS OF USE

(75) Inventor: Eric N. Olson, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/438,075

(22) Filed: Nov. 10, 1999

Related U.S. Application Data

(60) Provisional application No. 60/107,755, filed on Nov. 10, 1998, and provisional application No. 60/108,083, filed on Nov. 12, 1998.

(51) Int. Cl.$^7$ .................. A01K 67/027; A01K 67/00; A01K 67/033; G01N 33/00
(52) U.S. Cl. .................. 800/18; 800/3; 800/9; 800/13
(58) Field of Search ................ 800/18, 3, 21; 435/325, 455

(56) References Cited

FOREIGN PATENT DOCUMENTS

WO          WO 9405776 A        3/1994

OTHER PUBLICATIONS

Wall et al. Journal of Dairy Science 80:2213–24, Sep. 1997.*
Ebert et al. Molecular Endocrinology 2(3):277–83, Mar. 1988.*
Hammer et al. Journal of Animal Science 6(1):269–78, Jul. 1986.*
Mullins et al. Journal of Clinical Investigation 97(7):1557–1560, Apr. 1996.*
Qin et al. Journal of Biological Chemistry 272(40):25210–6, Oct. 1997.*
Wang et al. Circulation Research 86(4):478–84, Mar. 2000.*
Ross et al. Development 122(6):1799–809, Jun. 1996.*
Thai et al. Journal of Biological Chemistry 273(23):14285–92, Jun. 1998.*
Doud et al., "Adaptational response in transcription factors during development of myocardial hypertrophy," *Mol Cell Cardio*, 27:2359–2372, 1995.
Kolodziejczyk et al., "MEF2 is upregulated during cardiac hypertrophy and is required for normal post–natal growth of the myocardium," *Curr Biol*, 9:1203–1206, 1999.
Navankasattusas et al., "A ubiquitous factor (HF–1a) and a distinct muscle factor (HF–1b/MEF–2) form an e–box–independent pathways for cardiac muscle gene expression," *Mole. and Cell Biol*, 12:1469–1479, 1992.
Adolph et al., "Role of myocyte–specific enhancer–binder factor (MEF–2) in transcriptional regulation of the α–cardiac myosin heavy chain gene," *J. Biol. Chem.*, 268:5349–5352, 1993.

Bour et al., "Drosophila MEF2, a transcription factor that is essential for myogenesis," *Genes and Dev.*, 9:730–741, 1995.
Brand, "Myocyte enhancer factor 2 (MEF2)," *Int J. Biochem. Cell Biol.*, 29:1467–1470; 1997.
Clarke et al., "Epidermal Growth Factor Induction of the c–jun promoter by a rac pathway," *Mol. Cell Biol.*, 18:1065–1073, 1998.
Coso et al., "Signaling from G protein–coupled receptors to the c–jun promoter invovles the MEF2 transcription factor," *J. Biol. Chem.*, 272:20691–20697, 1997.
Edmondson et al., "MEF2 gene expression marks the cardiac and skeletal muscle lineages during mouse embryogenesis," *Development*, 120:1251–1263, 1994.
Gruver et al., "Targeted developmental overexpression of calmodulin induces proliferative and hypertrophic growth of cardiomyocytes in transgenic mice," *Endocrinology*, 133:376–388, 1993.
Han et al., "Activation of the transcription factor MEF2C by the MAP kinase p38 in inflammation," *Nature*, 386:296–299, 1997.
Herzig et al., "Angiotensin II type$_{1a}$ receptor gene expression in the heart: AP–1 and GATA–4 participate in the response to pressure overload," *Proc. Nat'l. Acad. Sci. USA*, 94:7543–7548, 1997.
Hongo et al., "Effect of stretch on contraction and the $Ca^{2+}$ transient in ferret ventricular muscles during hypoxia and acidosis," *Am. J. Physiol.*, 269:C690–C697, 1995.
Karns et al., "M–CAT, CarG, and Spl elements are required for $_1$ α–adrenergic induction of the skeletal α–actin promoter during cardiac myocyte hypertrophy," *J. Biol. Chem.*, 270:410–417, 1995.
Kato et al., "BMK1/ERK5 regulates serum–induced early gene expression through transcription factor MEF2C," *EMBO J.*, 16:054–06, 1997.
Kovacic–Milivojevic et al., "Selective regulation of the atrial natriuretic peptide gene by individual components of the activator protein–1 complex," *Endocrinology*, 137:1008–1117, 1996.

(List continued on next page.)

*Primary Examiner*—Deborah Crouch
*Assistant Examiner*—Joseph T. Woitach
(74) *Attorney, Agent, or Firm*—Fulbright & Jaworski, LLP

(57) ABSTRACT

The present invention relates to cardiac hypertrophy. More particularly, the present invention defines the molecular events linking calcium stimulation to cardiac hypertrophy. More specifically, the present invention shows that Ca++ stimulation of the hypertrophic response is mediated through MEF2. Thus, the present invention provides methods of treating cardiac hypertrophy as well as transgenic constructs for preparing transgenic animals. Further provided are methods of using the transgenic animals of the present invention, or cells isolated therefrom, for the detection of compounds having therapeutic activity toward cardiac hypertrophy.

17 Claims, 22 Drawing Sheets

(6 of 22 Drawing Sheet(s) Filed in Color)

OTHER PUBLICATIONS

Lee et al., "Myocyte–specific enhancer factor 2 and thyroid hormone receptor associate and synergistically activate the α–cardiac myosin heavy–chain gene," *Mol. Cell Biol.*, 17:2745–2755, 1997.

Leite et al., "Regulation of ANP secretion by endothelin–1 in cultured atrial myocytes: desensitization and receptor subtype," *Am. J. Physiol.*, 267:H2193–2203, 1994.

Lilly et al., "Requirement of MADS domain transcription factor D–MEF2 for muscle formation in Drosophila," *Science*, 267:688–693, 1995.

Lin et al., "Control of cardiac morphogenesis and myogenesis by the myogenic transcription factor MEF2C," *Science*, 276:1404–1407, 1997.

Liu et al., "Cyclosporin A–sensitive induction of the Epstein–Barr virus lytic switch is mediated via a novel pathway involving a MEF2 family member," *EMBO J.*, 16:143–153, 1997.

Martin et al., "Myocyte enhancer factor (MEF) 2C: A tissue–restricted member of the MEF–2 family of transcription factors," *Proc. Nat'l. Acad. Sci. USA*, 90:5282–5286, 1993.

Molkentin and Olson, "Combinatorial control of muscle development by bHLH and MADS–box transcription factors," *Proc. Nat'l. Acad. Sci. USA*, 93:9366–9373, 1996.

Molkentin and Olson, GATA4: a novel transcriptional regulator of cardiac hypertrophy?, *Circulation*, 96:3833–3835, 1997.

Molkentin et al., "Transcription factor GATA–4 regulates cardiac muscle–specific expression of the α–myosin heavy––chain gene," *Mol. Cell. Biol.*, 14:4947–4957, 1994.

Molkentin et al., "Cooperative activation of muscle gene expression by MEF2 and myogenic bHLH proteins," *Cell*, 83:1125–1136, 1995.

Molkentin et al., "Mutational analysis of the DNA binding, dimerization, and transcriptional activation of MEF2C," *Mol. Cell. Biol.*, 16:2627–2636, 1996.

Molkentin et al., "MEF2B is a potent transactivator expressed in early myogenic lineages," *Mol. Cell. Biol.*, 16:3814–3824, 1996.

Molkentin et al., "Phosphorylation of the MADS–box transcription factor MEF2C enhances its DNA binding activity," *J. Biol. Chem.*, 271:17199–17204, 1996.

Molkentin et al., "Requirement of the GATA4 Transcription factor for the heart tube formation and ventral morphogenesis," *Genes and Dev.*, 11:1061–1072, 1997.

Olson et al., "Regulation of muscle differentiation by the MEF2 family of MADS box transcription factors," *Developmental Biology*, 172:2–14, 1995.

Ostrove et al., "Inhibition of adenovirus–transformed cell oncogenicity by adeno–associated virus," *Virology*, 113:521–533, 1981.

Sadoshima and Izumo, "Signal transduction pathways of angiotensin II–induced c–fos gene expression in cardiac myocytes in vitro," *Circ. Res.*, 73:424–438, 1993.

Sadoshima and Izumo, "The cellular and molecular response of cardiac myocytes to mechanical stress," *Ann. Rev. Physiol.*, 59:551–571, 1997.

Sadoshima et al., "Autocrine release of angiotensin II mediates stretch–induced hypertrophy of cardiac myocytes in vitro," *Cell*, 75:977–984, 1993.

Woronicz et al., "Regulation of the Nur77 orphan steroid receptor in activation–induced apoptosis," *Mol. Cell. Biol.* 6364–6367, 1995.

Zou et al., "Protein Kinase C, but not tyrosine kinases of ras, plays a critical role in angiotensin ii–induced activation of Raf–1 Kinase and extracellular signal–related protein kinases in cardiac myocytes," *J. Biol. Chem.*, 271:33592–33597, 1996.

* cited by examiner

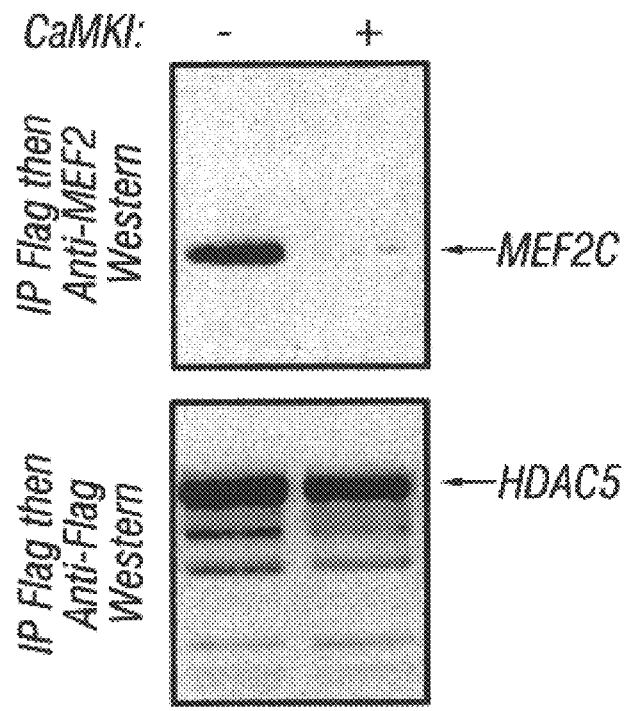
FIG. 15B
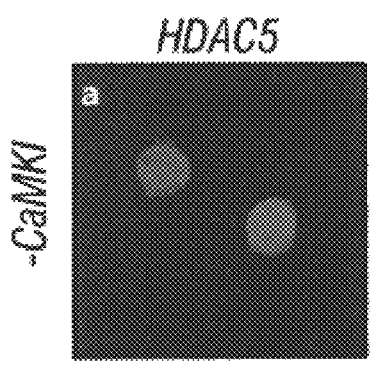
FIG. 15C-a
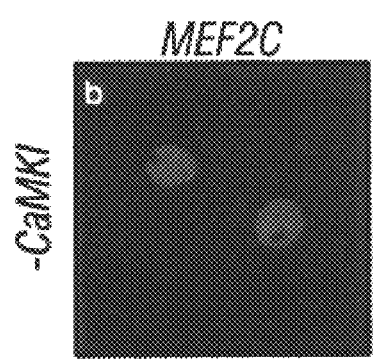
FIG. 15C-b
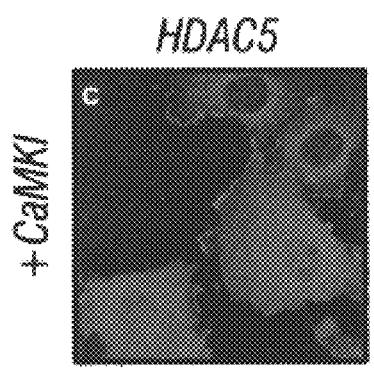
FIG. 15C-c
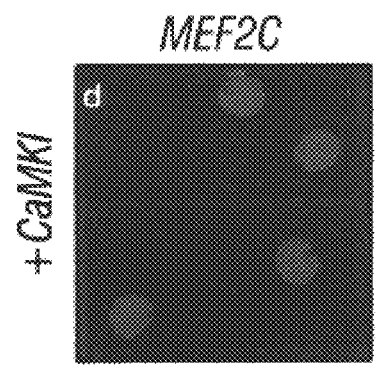
FIG. 15C-d

TRANSGENIC MOUSE COMPRISING A MEF2 BINDING SITE OPERATIVELY LINKED TO AN INDICATOR GENE AND METHODS OF USE

This application claims priority to and specifically incorporates by reference, the content of U.S. Provisional Application Serial No. 60/107,755 filed Nov. 10, 1998 and U.S. Provisional Application Serial No. 60/108,083 filed Nov. 12, 1998. The entire text of each of the above-referenced disclosures is specifically incorporated by reference herein without disclaimer.

BACKGROUND OF THE INVENTION

1. Field of the Invention

The present invention relates generally to the field of molecular biology. More particularly, it concerns the discovery of a central mediator of cardiac hypertrophy.

2. Description of Related Art

Cardiac hypertrophy is an adaptive response of the heart to virtually all forms of cardiac disease, including those arising from hypertension, mechanical load, myocardial infarction, cardiac arrythmias, endocrine disorders and genetic mutations in cardiac contractile protein genes. While the hypertrolic response is initially a compensatory mechanism that augments cardiac output, sustained hypertrophy can lead to dilated cardiomyopathy, heart failure, and sudden death. In the United States, approximately half a million individuals are diagnosed with heart failure each year, with a mortality rate approaching 50%.

Despite the diverse stimuli that lead to cardiac hypertrophy, there is a prototypical molecular response of cardiomyocytes to hypertrophic signals that involves an increase in cell size and protein synthesis, enhanced sarcomeric organization, upregulation of fetal cardiac genes, and induction of genes such as c-fos and c-myc (reviewed in Chien et al., 1993, Sadoshima and Izumo, 1997). The causes and effects of cardiac hypertrophy have been documented extensively, but the underlying molecular mechanisms that couple hypertrophic signals, initiated at the cell membrane to reprogram cardiomyocyte gene expression remain poorly understood. Elucidation of these mechanisms is a central issue in cardiovascular biology and is critical in the design of new strategies for prevention or treatment of cardiac hypertrophy and heart failure.

Numerous studies have implicated intracellular $Ca^{++}$ as a signal for cardiac hypertrophy. In response to myocyte stretch or increased loads on working heart preparations, intracellular $Ca^{++}$ concentrations increase (Marban et al., 1987; Bustamante et al., 1991; Hongo et al., 1995). This is consistent with a role of $Ca^{++}$ in coordinating physiologic responses with enhanced cardiac output. A variety of humoral factors, including angiotensin II (AngII), phenylephrine (PE) and endothelin-1 (ET-1), which induce the hypertrophic response in cardiomyocytes (Karliner et al., 1990; Sadoshima and Izumo, 1993a, 1993b; Leite et al., 1994), also share the ability to elevate intracellular $Ca^{++}$ concentrations.

Hypertrophic stimuli result in reprogramming of gene expression in the adult myocardium such that genes encoding fetal protein isoforms like β-myosin heavy chain (MHC) and α-skeletal actin are upregulated, whereas the corresponding adult isoforms, α-MHC and α-cardiac actin, are downregulated. The natriuretic peptides, atrial natriuretic factor (ANF) and β-type natriuretic peptide (BNP), which decrease blood pressure by vasodilation and natriuresis, also are rapidly upregulated in the heart in response to hypertrophic signals (reviewed in Komuro and Yazaki, 1993). The mechanisms involved in coordinately regulating these cardiac genes during hypertrophy are unknown, although binding sites for several transcription factors, including serum response factor (SRF), TEF-1, AP-1, and Sp1 are important for activation of fetal cardiac genes in response to hypertrophy (Sadoshima and Izumo, 1993a; 1993b; Kariya et al., 1994; Karns et al., 1995; Kovacic-Milivojevic et al., 1996). Most recently, the cardiac-restricted zinc finger transcription factor GATA4 also has been shown to be required for transcriptional activation of the genes for Ang II type 1α receptor and β-MHC during hypertrophy (Herzig et al., 1997; Hasegawa et al., 1997; reviewed in Molkentin and Olson, 1997).

The potential roles of the myocyte enhancer factor-2 (MEF2) family of transcription factors in cardiac development and hypertrophy are also considered. There are four members of the MEF2 family, referred to as MEF2A, -B, -C, and -D, in vertebrates (reviewed in Olson et al., 1995). These transcription factors share homology in an N-terminal MADS-box and an adjacent motif known as the MEF2 domain. Together, these regions mediate DNA binding, homo- and heterodimerization, and interaction with various cofactors, such as the myogenic bHLH proteins in skeletal muscle. MEF2 binding sites, $CT(A/T)_4TAG/A$, are found in the control regions of the majority of skeletal, cardiac, and smooth muscle genes. The C-termini of the MEF2 factors function as transcription activation domains and are subject to complex patterns of alternative splicing.

During mouse embryogenesis, the MEF2 genes are expressed in precursors of cardiac, skeletal and smooth muscle lineages and their expression is maintained in differentiated muscle cells (Edmondson et al. 1994). The MEF2 factors are also expressed at lower levels in a variety of nonmuscle cell types. Targeted inactivation of MEF2C has been shown to result in embryonic death at about E9.5 due to heart failure (Lin et al., 1997). In the heart tubes of MEF2C mutant mice, several cardiac genes fail to be expressed, including a-MHC, ANF, and a-cardiac actin, whereas several other cardiac contractile protein genes are expressed normally, despite the fact that they contain essential MEF2 binding sites in their control regions. These results have demonstrated the essential role of MEF2C for cardiac development and suggest that other members of the MEF2 family may have overlapping functions that can support the expression of a subset of muscle genes in the absence of MEF2C. In Drosophila, there is only a single MEF2 gene, called D-MEF2. In embryos lacking D-MEF2, no muscle structural genes are activated in any myogenic lineage, demonstrating that MEF2 is an essential component of the differentiation programs of all muscle cell types (Lilly et al., 1995; Bour et al., 1995).

Although MEF2 factors are required for activation of muscle structural genes, they are not sufficient to activate these genes alone. Instead, biochemical and genetic studies have shown that MEF2 factors act combinatorially with other transcription factors to activate specific programs of gene expression. In skeletal muscle, MEF2 establishes a combinatorial code through interaction with members of the MyoD family to activate muscle gene transcription (Molkentin et al., 1995; Molkentin and Olson, 1996). The specific partners for MEF2 in cardiac and smooth muscle cells or in nonmuscle cells in which MEF2 proteins have been shown to regulate a variety of genes remain to be defined.

As discussed below, there are four lines of evidence that suggest an important role for MEF2 in the control of cardiac hypertrophy. 1) MEF2 regulates many of the fetal cardiac genes that are up-regulated during hypertrophy. 2) MEF2 transcriptional activity is induced by the same signal transduction pathways that control hypertrophy. 3) MEF2C is upregulated in the hearts of human patients with congestive heart failure. 4) MEF2 synergizes with the thyroid hormone receptor to regulate transcription of the a-MHC gene (Lee et al., 1997) and thyroid hormone is a potent inducer of hypertrophy.

Transcriptional activation of the orphan steroid receptor Nur77 gene (NGFI-B) in T cells in response to T cell receptor activation is mediated by a CsA-sensitive, calcium-dependent signaling pathway (Woronicz et al., 1995). This signaling pathway is directed at two MEF2 binding sites in the NGFI-B promoter. There is no change in DNA binding activity of MEF2 in the presence or absence of calcium signals in that system, whereas transcriptional activity of MEF2 is dramatically increased by calcium signaling. This implies that calcium signals must enhance MEF2 activity by inducing a cofactor or a posttranslational modification of MEF2 that stimulates transcriptional activity.

In addition, transcription of the calcium-dependent lytic cycle switch gene BZLF1, which is required for induction of the lytic cycle of Epstein-Barr virus (EBV), is inhibited by CsA and FK506, indicating that a calcineurin-dependent pathway mediates activation of this gene (Liu et al., 1997). CsA-sensitivity of BZLF1 transcription maps to three MEF2 sites in the BZLF1 promoter. CsA-sensitive inducibility was shown to be reconstituted using an artificial promoter containing multiple copies of the MEF2 site in conjunction with a CREB/AP-1 site. NFAT did not bind the BZLF1 promoter, but CsA-sensitive induction of this promoter was shown to be calcineurin- and NFAT-dependent. CaMKIV was also shown to be a potent inducer of MEF2 activity (Liu et al., 1997). The mechanism whereby MEF2 confers responsiveness to the calcineurin/NFAT signaling system remains to be elucidated.

The MAP kinase signaling pathway has also been shown to lead to enhanced transcriptional activity of MEF2 factors in a variety of cell types (Han et al., 1997; Coso et al., 1997; Kato et al., 1997. Clarke et al., 1998). This enhancement has been shown for MEF2C to be mediated by phosphorylation of three amino acids, Thr293, Thr300, and Ser387, in the C-terminal activation domain by the MAP kinase family member p38. Whether these same residues are phosphorylated by hypertrophic signaling in the heart remains to be determined.

It is clear that the cardiac hypertrophic response is somehow initiated through a $Ca^{++}$ dependent pathway. However, the precise identification of the gene(s) which mediate(s) the hypertrophic response remains elusive. The present invention is directed toward the elucidation of the exact point in the hypertrophic pathway which may be manipulated to achieve beneficial effects on cardiac hypertrophy. In order to develop pharmacologic strategies for treatment of cardiac hypertrophy in humans, it will be important to establish animal models which accurately reflect the pathological profile of the disease.

SUMMARY OF THE INVENTION

Thus, there is provided, in accordance with the present invention, a method of treating hypertrophy in a cardiomyocyte cell comprising the step of inhibiting the function of MEF2. Inhibiting the function of MEF2 may comprise reducing the expression of MEF2, for example, by contacting MEF2 with an agent that binds to and inactivates MEF2. The method further comprises inhibiting the upregulation of a gene upregulated by MEF2, for example, by antisense. The agent that reduces the expression of MEF2 may be an antisense construct, and the agent that binds to and inactivates MEF2 may be an antibody preparation, for example, a single chain antibody, or a small molecule inhibitor.

In another embodiment, there is provided a transgenic, non-human mammal, the cells of which comprise an indicator gene under the control of a transcriptional regulatory element, wherein said transcriptional regulatory element is activated by MEF2. The mammal may be a mouse, rat, guinea pig, pig, sheep, or other suitable animal. The indicator gene may be selected from the group consisting of lacZ, a gene encoding green fluorescent protein and a gene encoding luciferase.

In still another embodiment, there is provided a method for screening modulators of cardiac hypertrophy comprising the steps of (a) providing a cardiomyocyte that contains an indicator gene under the control of MEF2-inducible regulatory sequences; (b) contacting said cell with a candidate modulator; and (c) monitoring said cell for expression of said indicator gene as compared to a cell not treated with said candidate modulator.

The cell may be derived from a cardiomyocyte cell line or a primary cardiomyocyte. The cell also may be derived from a transgenic animal. The contacting may be performed in vitro or in vivo. The candidate modulator may be an antisense construct, from a small molecule library or an antibody (e.g., a single chain antibody).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The file of this patent contains at least one drawing executed in color. Copies of this patent with color drawings will be provided by the Patent and Trademark Office upon request and payment of the necessary fee.

FIG. 12A, cells were stimulated with PE (10 uM) or 10% FBS, as indicated, and expression of the MEF2-dependent reporter, 3×MEF2-luciferase, was assayed. FIG. 12B, cells transiently transfected with pG5E1b-luciferase (Gal-luc) and GAL-MEF2C were stimulated with PE, as in FIG. 12A, in the presence of KN62 or SB202190, as indicated. FIG. 12C, cells were transiently transfected with pG5E1b-luciferase and GAL-MEF2C (left panel) or GAL-MEF2C-ΔN (right panel) along with activated CaMKIV and MKK6, as indicated.

FIG. 13A, induction of MEF2 activity by CaMKIV in the intact heart. MEF2 indicator mice were bred with mice harboring an α-MHC-CaMKIV or α-MHC-MEK5 transgene, as described in the text. Littermates positive for the lack transgene and lacking (left) or containing the CaMKIV (middle) or MEK5 (right) transgene were sacrificed at 8 weeks of age and hearts were stained for lacZ expression. LacZ expression is detected throughout the CaMKIV transgenic heart, but not in the control littermate or in an α-MHC-MEK5 transgenic, demonstrating that MEF2 activation is a downstream step in the CaMKIV signaling pathway in vivo. FIG. 13B, nuclear extracts were prepared from hearts of nontransgenic and α-MHC-CaMKIV transgenic littermates and used for gel mobility shift assays with a $^{32}$P-labeled MEF2 site as probe. Anti-MEF2A antibody was added to assays as indicated. Comparable amounts of MEF2 DNA binding activity were detected in both extracts and all activity was supershifted with anti-MEF2A antibody. Nonimmune serum had no effect on the MEF2-DNA protein complex. Only the region of the gel containing the shifted probe in shown.

FIG. 14A, schematic diagrams of HDACs 4 and 5 and the different regions of the proteins encoded by cDNAs rescued as "prey" in two-hybrid screens are shown. The rescued HDAC cDNAs overlap in the 18-amino acid segment shown at the bottom. FIG. 14B, MEF2C and HDACs 4 and 5 from transfected cells. HDACs with Flag epitopes at their carboxyl-termini and MEF2C were expressed in transiently transfected 293 T cells. Forty eight hours following transfection, cell extracts were prepared and immunoprecipitated with anti-Flag antibody. Immunoprecipitates were then separated by SDS-PAGE and sequentially immunoblotted with anti-MEF2 or anti-Flag antibodies. The top panel shows the results of anti-MEF2 Western and demonstrates specific interaction of HDAC 4 and 5 with MEF2C. The bottom panel shows the results of anti-Flag (HDAC) Western blot and demonstrates that comparable amounts of each HDAC were expressed in transfected cells. FIG. 14C, 10T1/2 cells were transiently transfected with pG5E1b-luciferase reporter and expression vectors for GAL4-MEF2C, GAL4-MEF2C-ΔN, and the indicated HDACs and luciferase activity was determined. FIG. 14D, binding of a MEF2-DNA complex to GST-HDAC4. GST-HDAC4 was incubated with $^{35}$S-labeled in vitro translation products, which were premixed with a $^{32}$P-labeled MEF2 site. Beads were then washed and associated radioactivity was determined.

FIG. 15A, FIG. 15B, FIG. 15C and FIG. 15D. CaM kinase signaling overcomes HDAC-mediated repression of MEF2 activity. 10T1/2 cells were transiently transfected with pG5E1b-luciferase and the indicated expression vectors and luciferase activity was determined. FIG. 15B, immunoprecipitations from extracts of cells transfected with MEF2C, HDAC4 and CaMKI expression vectors, as indicated, were performed as described in FIG. 3B. In the presence of activated CaMKI, interaction between MEF2C and HDAC5 was significantly diminished. FIG. 15C, Cos cells cotransfected with expression vectors encoding Flag-tagged HDAC5 and Myc-tagged MEF2C in the absence (a and b) or presence (c and d) of a CaMKI expression plasmid were fixed and examined by indirect immunofluorescence using rhodamine-conjugated anti-Flag and fluorescein-conjugated anti-Myc antibody. Images are from doubly-stained cultures viewed at different wavelengths. FIG. 15D, a model for the regulation of MEF2 activity by CaMK and MAPK signaling.

FIG. 16A, MEF2 factors and HDACs 4 and 5 were coimmunoprecipitated from transfected cells as described. HDACs with Flag epitopes at their carboxyl-termini and MEF2C were expressed in transiently transfected 293 T cells. Forty eight hours following transfection, cell extracts were prepared and immunoprecipitated with anti-Flag antibody. Immunoprecipitates were then separated by SDS-PAGE and sequentially immunoblotted with anti-MEF2 or anti-Flag antibodies. The top panel shows the results of anti-MEF2 Western and demonstrates specific interaction of HDAC 4 and 5 with MEF2A and D. The bottom panel shows the results of anti-Flag (HDAC) Western blot and demonstrates that comparable amounts of each HDAC were expressed in transfected cells. A schematic of the experiment is shown on the side. In FIG. 16B, cells extracts were immunoprecipitated with anti-Flag antibody followed by Western blot with anti-MEF2 (top panel) or were probed by anti-MEF2 Western without prior immunoprecipitation (lower panel). Deletion of the HDAC5 amino-terminus prevents interaction with MEF2A and MEF2C.

DESCRIPTION OF ILLUSTRATIVE EMBODIMENTS

Figure 1:
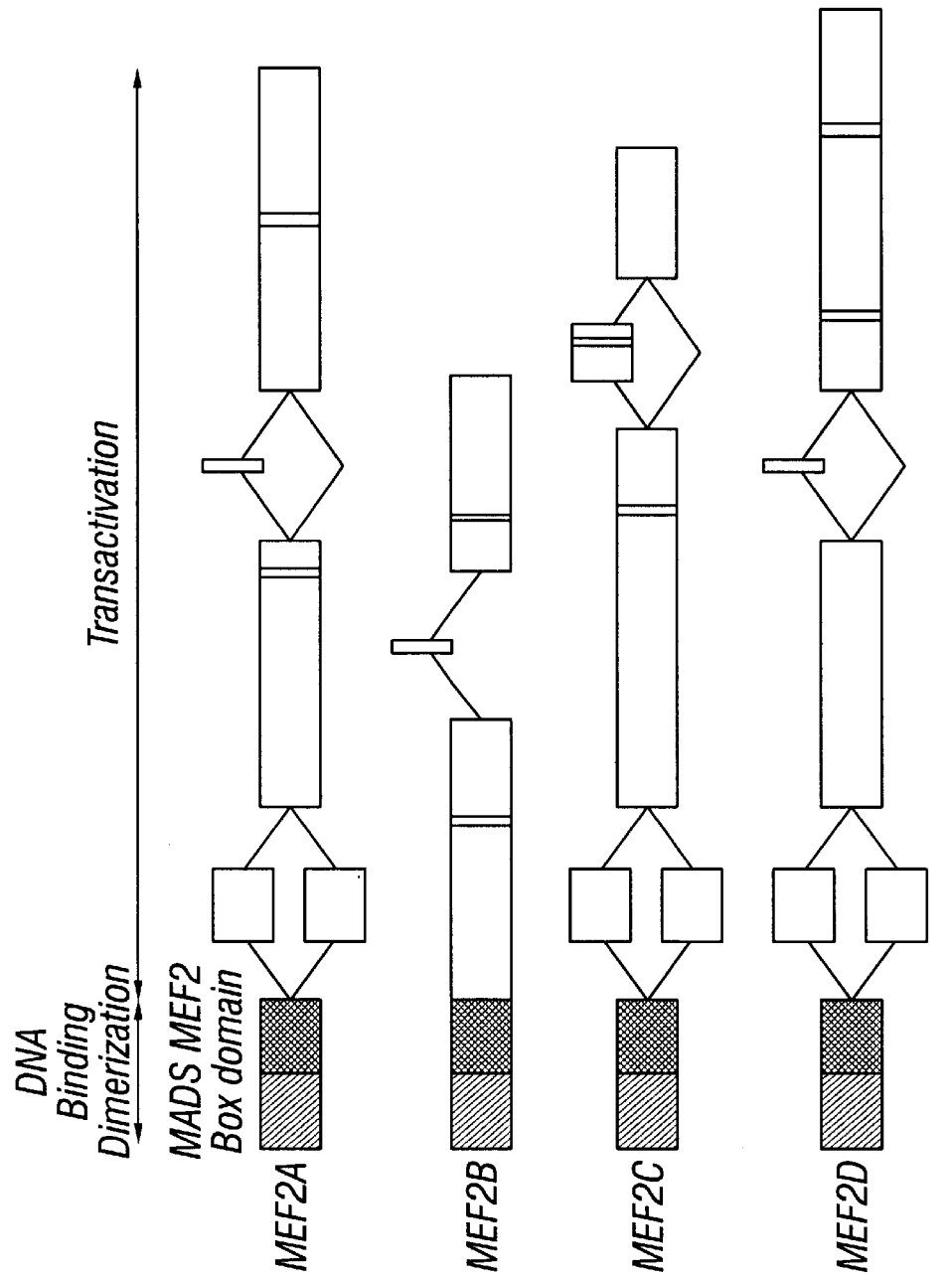
FIG. 1. Schematic diagrams of the MEF2 isoforms.
Figure 2:
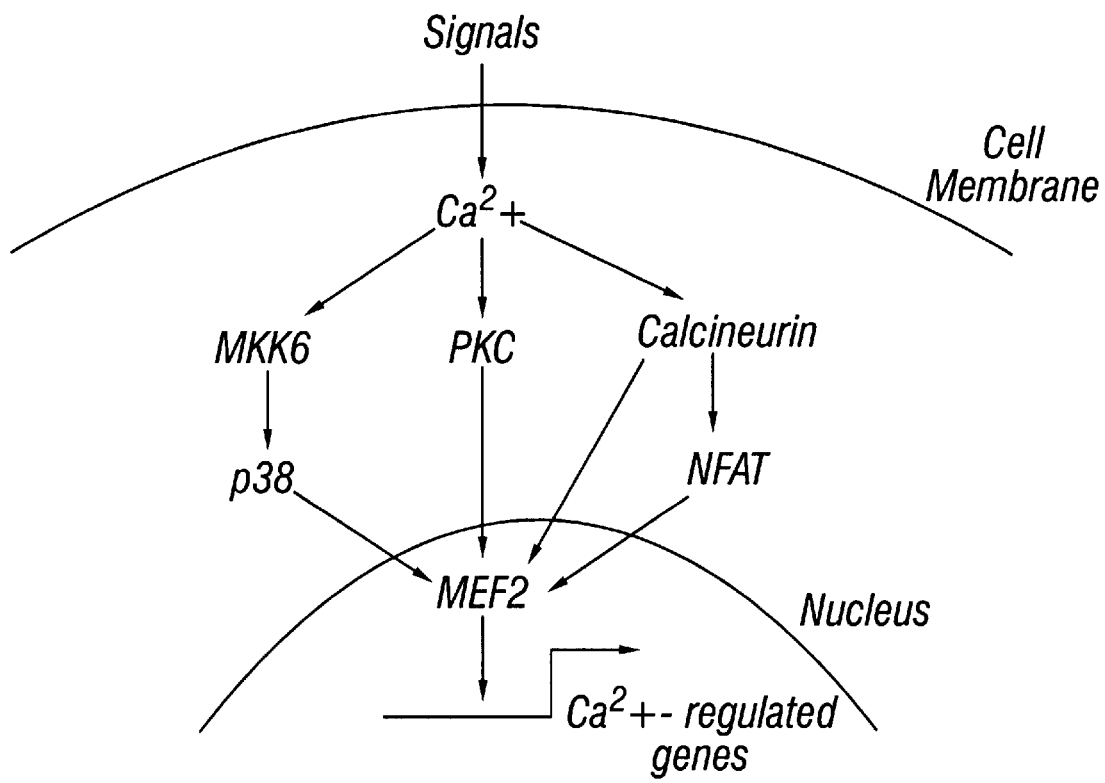
FIG. 2. Calcium-dependent signaling systems that regulate MEF2 activity. A variety of extracellular stimuli result in elevation of intracellular calcium, which activates multiple intracellular signaling systems, including calcineurin, CAM kinases, PKC, and MAP kinases. All of these signals activate MEF2 and result in cardiac hypertrophy.

Cardiac hypertrophy, which results in heart failure, is a major cause of morbidity in the United States, but the underlying molecular mechanisms are not understood. Hypertrophic cardiomyopathy occurs in both familial and sporadic forms. This type of cardiomyopathy is characterized by hypertrophy of the left ventricle. Hypertrophic cardiomyopathy is characterized by enhanced systolic function, a prolonged and abnormally powerful isometric contraction phase followed by impaired relaxation and increased chamber stiffness during diastole.

Cardiac hypertrophy in response to an increased workload imposed on the heart is a fundamental adaptive mechanism. It is a specialized process reflecting a quantitative increase in cell size and mass (rather than cell number) as the result of any or a combination of neural, endocrine or mechanical stimuli. Hypertension, another factor involved in cardiac hypertrophy, is a frequent precursor of congestive heart failure. When heart failure occurs, the left ventricle usually is hypertrophied and dilated and indices of systolic function, such as ejection fraction, are reduced. Clearly, the cardiac hypertrophic response is a complex syndrome and the elucidation of the pathways leading to cardiac hypertrophy will be beneficial in the treatment of heart disease resulting from a variety of stimuli.

1. The Present Invention

It is well established that elevation in intracellular $Ca^{++}$ is associated with the initiation of mechanical or agonist-induced cardiac hypertrophy (Marban et al. 1987; Bustamante et al., 1991; Hongo et al., 1995; Le Guennec et al., 1991; Perreault et al., 1994; Saeki et al., 1993). Further, it is known that cardiac hypertrophy results from the up-regulation of certain genes, which leads to an increase in the protein content of cardiomyocytes with little or no increase in the number of cells. Activation of this hypertrophic pathway, results in molecular and pathophysiologic changes. Exploiting these interactions, both in diagnostic and therapeutic contexts is the basis of the invention as described herein below.

The present invention provides transgenic mice that demonstrate MEF2 action in the heart by activation of a lacZ transgene. More particularly, these mice are created using a transgene in which three tandem copies of the MEF2 site from the desmin gene are cloned upstream of the heat shock protein (hsp)-68 promoter, which is expressed at a basal level in all cells, and a lacZ reporter. During embryogenesis, the MEF2 site-dependent transgene is expressed in developing muscle cell lineages, consistent with the importance of MEF2 factors for the activation of cardiac, skeletal and smooth muscle gene expression. However, after birth, expression of the transgene is downregulated to levels that are undetectable by colorimetric lacZ tissue staining.

To test the response of the MEF2-lacZ transgene to hypertrophic signals in the heart, the transgene is introduced by breeding into strains of mice bearing MHC-calcineurin and MHC-CAMKIV transgenes. The expression of lacZ is dramatically upregulated in response to calcineurin and CAMKIV, indicating activation of the hypertrophic response.

It has been observed that PKC activity is associated with MEF-2 activation, raising the possibility that the phosphorylation state of MEF-2 is directly related to its activity. As such, it may be possible to construct mutant forms of MEF-2 which are constitutively activated by engineering the molecules to appear, to target molecules, as though they are phosphorylated. Transgenic cells and animals which contain such mutant MEF-2 genes may then be used as disease models, both from the standpoint point of understanding the cellular, tissue and organ pathophysiology of cardiac hypertrophy, and in the testing of drugs which may limit the MEF2 related activation of hypertrophic genes. It is also desired to identify genes that are downstream of the MEF2 target gene responsible for cardiac hypertrophy.

The present invention further provides methods of MEF2 gene knockout. By gene targeting, the four MEF2 genes in ES cells and transgenic mice were inactivated. In particular, mice lacking MEF2C die at E9.5 from severe cardiovascular defects that include the absence of a right ventricle and the failure of the vascular system to form (Lin et al., 1997). In addition, a subset of cardiac protein genes, including a-MHC, a-cardiac actin and ANF, fail to be expressed in the developing heart of these animals. In contrast, several cardiac genes, such as myosin light chains 2A and 2V, are expressed at normal levels in the hearts of MEF2C mutant embryos, indicating that they are MEF2C-independent.

The present invention further contemplates the use of an active MEF2 gene producing MEF2 polypeptide. A possible mode of constitutive gene expression is the fusion of the MEF2 gene to a transcriptional active domain of an active transcription factor.

2. A Transcriptional Pathway for Cardiac Hypertrophy

Figure 11:
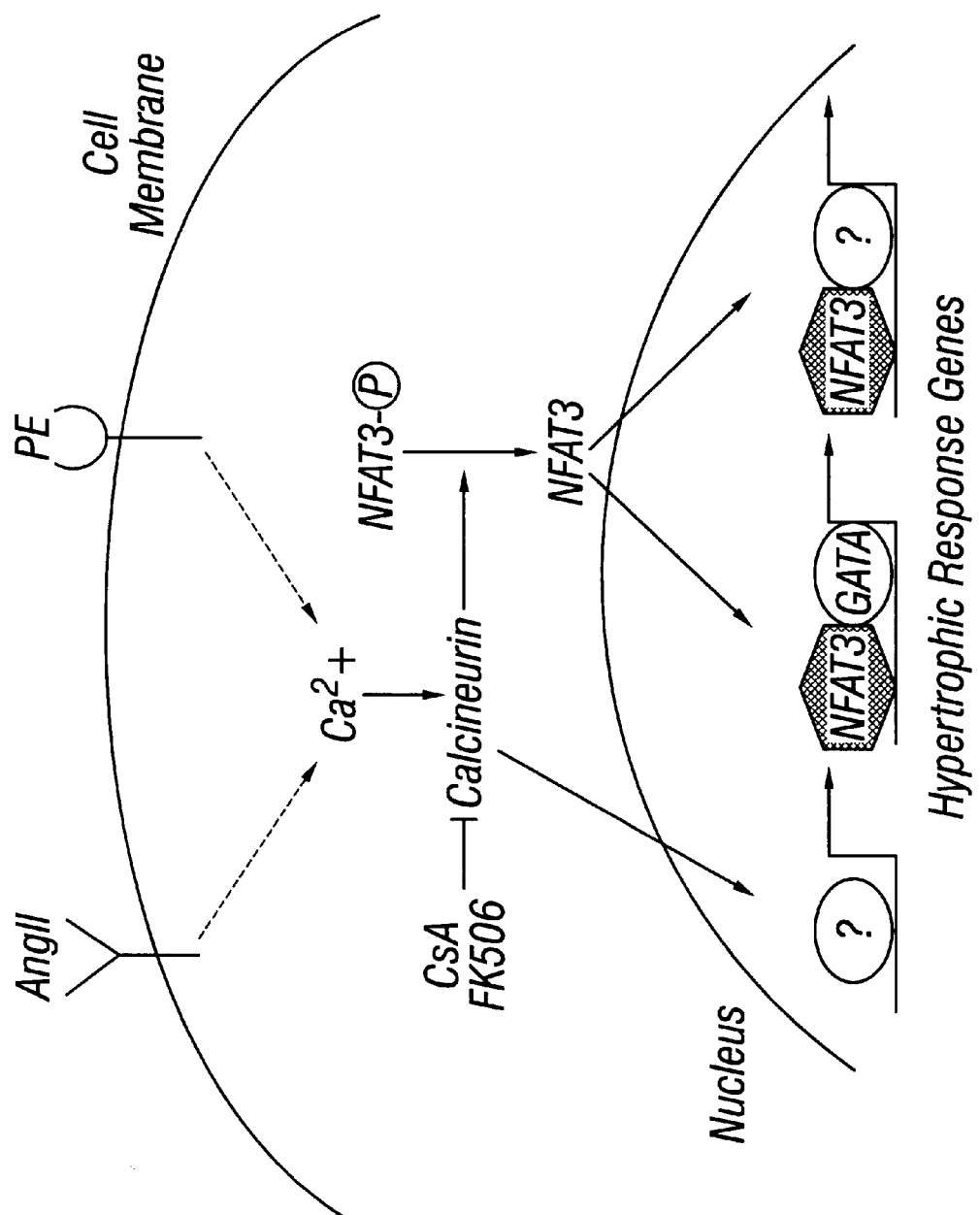
FIG. 11. A pathway for hypertrophic signaling by calcineurin and NFAT3. AngII and PE, and possibly other hypertrophic stimuli, acting at the cell membrane lead to the activation of calcineurin in the cytoplasm. Calcineurin dephosphorylates NFAT3, resulting in its translocation to the nucleus, interaction with GATA4, and activation of fetal cardiac genes. In principle, calcineurin or NFAT3 could act through GATA4-independent mechanisms.

As stated above it is known that $Ca^{++}$ activation is involved in cardiac hypertrophy, remarkably, however, the possibility that calcineurin might participate in the transduction of hypertrophic signals in cardiomyocytes has not been previously investigated. The present invention describes a calcineurin dependent pathway for cardiac hypertrophy, this pathway is depicted in FIG. 11. The individual components of this pathway as they relate to cardiac hypertrophy are discussed in further detail herein below.

a. Calcineurin

Calcineurin is a ubiquitously expressed serine/threonine phosphatase that exists as a heterodimer, comprised of a 59 kD calmodulin-binding catalytic A subunit and a 19 kD $Ca^{++}$—binding regulatory B subunit (Stemmer and Klee, 1994; Su et al., 1995). Calcineurin is uniquely suited to mediate the prolonged hypertrophic response of a cardiomyocyte to $Ca^{++}$ signaling because the enzyme is activated by a sustained $Ca^{++}$ plateau and is insensitive to transient $Ca^{++}$ fluxes as occur in response to cardiomyocytc contraction (Dolmetsch et al., 1997).

Activation of calcineurin is mediated by binding of $Ca^{++}$ and calmodulin to the regulatory and catalytic subunits, respectively. Previous studies showed that over-expression of calmodulin in the heart also results in hypertrophy, but the mechanism involved was not determined (Gruver et al., 1993). Given the observations presented herein, it is now clear that calmodulin acts through the calcineurin pathway to induce the hypertrophic response.

b. MEF2

A family of transcription factors, the monocyte enhancer factor-2 family (MEF2), are known to play an important role in morphogenesis and myogenesis of skeletal, cardiac, and smooth muscle cells (Olson et al., 1995). MEF2 factors are expressed in all developing muscle cell types, binding a conserved DNA sequence in the control regions of the majority of muscle-specific genes. Of the four mammalian MEF2 genes, three (MEF2A, MEF2B and MEF2C) can be alternatively spliced, which have significant functional differences (Brand, 1997; Olson et al., 1995). These transcription factors share homology in an N-terminal MADS-box and an adjacent motif known as the MEF2 domain. Together, these regions of MEF2 mediate DNA binding, homo- and heterodimerization, and interaction with various cofactors, such as the myogenic bHLH proteins in skeletal muscle. Additionally, biochemical and genetic studies in vertebrate and invertebrate organisms have demonstrated that MEF2 factors regulate myogenesis through combinatorial interactions with other transcription factors.

Loss-of-function studies indicate that MEF2 factors are essential for activation of muscle gene expression during embryogenesis. The expression and functions of MEF2 proteins are subject to multiple forms of positive and negative regulation, serving to fine-tune the diverse transcriptional circuits in which the MEF2 factors participate. The present invention describes methods for determining the role(s) of MEF2 in the development of cardiac hypertrophy.

c. Inhibitors of Calcineurin

CsA and FK-506, bind the immunophilins cyclophilin and FK-506-binding protein (FKBP12), respectively, forming complexes that bind the calcineurin catalytic subunit and inhibit its activity. CsA and FK-506 block the ability of cultured cardiomyocytes to undergo hypertrophy in response to AngII and PE. Both of these hypertrophic agonists have been shown to act by elevating intracellular $Ca^{++}$, which results in activation of the PKC and MAP kinase signaling pathways (Sadoshima and Izumo, 1993a, 1993b; Kudoh et al., 1997; Yamazaki et al., 1997, Zou et al., 1996). CsA does not interfere with early signaling events at the cell membrane, such as PI turnover, $Ca^{++}$ mobilization, or PKC activation (Emmel et al., 1989). Thus, its ability to abrogate the hypertrophic responses of AngII and PE suggests that calcineurin activation is an essential step in the AngII and PE signal transduction pathways.

d. Hypertrophic Genes

In response to hormonal, genetic and mechanical stimuli, the myocardium adapts to increased workloads through the hypertrophy of individual muscle cells (Morgan et al. 1987). Because the adult myocardial cell is terminally differentiated and has lost the ability to proliferate, cardiac growth during the hypertrophic process results primarily from an increase in protein content per individual myocardial cell, with little or no change in muscle cell number. Thus, the central features of the myocardial hypertrophic response are increase in contractile protein content, the induction of contractile protein isoforms and the expression of embryonic markers, which appear to depend largely on the activation of transcription of the corresponding cardiac gene that encode these proteins.

Up-regulation of contractile protein genes constitutively expressed in the myocardium, such as the rat cardiac myosin light chain-2 (MLC-2) gene, results in a quantitative increase in MLC-2 levels and a corresponding accumulation of this contractile protein in individual myocardial cells. Myocardial cell hypertrophy also is associated with qualitative changes in contractile protein composition, including the induction of contractile protein genes that are normally expressed in embryonic development, e.g., the reactivation of skeletal α-actin (Schwartz et al. 1986) and β-myosin heavy-chain (MHC) expression in rodent and rabbit models of cardiac hypertrophy. In addition to the induction of specific contractile protein components, ventricular hypertrophy is also characterized by alterations in the expression of noncontractile protein genes.

Of the known noncontractile protein genes that are up-regulated during, ventricular hypertrophy, the reactivation of atrial natriuretic factor (ANF) expression may be the best characterized. ANF is a vasoregulatory peptide hormone which is secreted by atrial myocytes, is stored within secretory granules which undergo exocytosis in response to stretch of the tissue, or to hormones such as catecholamines or endothelin (ET). The β-type natriuretic peptide (BNP), which decrease blood pressure by vasodilation and natriuresis, also is rapidly upregulated in the heart in response to hypertrophic signals (reviewed in Komuro and Yazaki, 1993).

3. Methods of Making Transgenic Mice

As noted above, a particular embodiment of the present invention provides transgenic animals which contain MEF2 related constructs. Transgenic animals expressing MEF2 regulated transgenes, recombinant cell lines derived from such animals and transgenic embryos may be useful in methods for screening for and identifying agents that repress function of MEF2 and thereby alleviate cardiac hypertrophy. The use of constitutively expressed MEF2 genes that are fused to a transcriptionally active domain will additionally be useful. Also, transgenic animals which are "knocked out" for MEF2 expression will find use in analysis of developmental aspects of MEF2 function. Further, the "knocked out" mice can be utilized in identifying downstream MEF2 targets using differential display.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which express an indicator polypeptide that is regulated by MEF2.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris,pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. *Manipulating the Mouse Embryo* (Cold Spring Harbor Laboratory, Cold Spring Harbor, N.Y., 1986), in Palmiter et al. *Nature* 300:611 (1982); in *The Qiagenologist, Application Protocol*, 3rd edition, published by Qiagen, Inc., Chatsworth, Calif.; and in Sambrook et al. *Molecular Cloning: A Laboratory Manual* (Cold Spring Harbor Laboratory, Cold Spring Harbor. N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% averting per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

As noted above, transgenic animals and cell lines derived from such animals may find use in certain testing experiments. In this regard, transgenic animals and cell lines expressing MEF2 regulated indicator genes may be exposed to test substances. These test substances can be screened for the ability to decrease MEF2 activity. Compounds identified by such procedures will be useful in the treatment of heart disease.

4. Transgenic Mice and Their Use

The transgenic animals of the present invention include those which have a substantially increased probability of spontaneously developing cardiac hypertrophy, when compared with non-transgenic littermates. A "substantially increased" probability of spontaneously developing cardiac hypertrophy means that a statistically significant increase of measurable symptoms of cardiac hypertrophy is observed when comparing the transgenic animal with non-transgenic littermates.

In one embodiment, the transgenic animals of the present invention are produced with transgenes which comprise a coding region that encodes a gene product which modulates transcription of at least one gene that is expressed in cardiomyocytes in response to a hypertrophic signal. In addition, the use of transgenic "identifier animals," which comprise an indicator gene under the control of a transcriptional regulatory element that is activated by MEF2, can be used to screen for MEF2 activity.

As used herein, the term "hypertrophic signal" indicates any stimulus, mechanical or chemical, which results in measurable symptoms of cardiac hypertrophy. Hypertrophic signals include, but are not limited to, mechanical stretch, β-adrenergic agonists, $\alpha_1$-adrenergic receptor agonists and angiotensin II. Symptoms of cardiac hypertrophy can be measured by various parameters including, but not limited to, left ventricular mass/body weight, changes in cardiomyocyte size and organization, changes in cardiac gene expression and changes in cardiac function.

The transgenic mouse of the present invention has a variety of different uses. First, by creating an animal model in which MEF2 activity can be measured, the present inventors have provided a living "vessel" in which the function of MEF2 may be further dissected. In one particular scenario, the transgenic mouse may be used to elucidate the interactions of MEF2 with additional nuclear factors. Thus, clearly, the present invention also encompasses isolation of a nuclear factors that act via an interaction with MEF2.

Another use for the transgenic mouse of the present invention is in the in vivo identification of a modulator of MEF2 activity, and ultimately of cardiac hypertrophy. The presence of a MEF2 regulated indicator gene represents a baseline for MEF2 function. Treatment of a transgenic mouse with a putative MEF2 inhibitor, and comparison of the response of this treated mouse with the untreated transgenic animal, provides a means to evaluate the activity of the candidate inhibitor.

5. Treatment of Heart Disease

Though there have been reports that a $Ca^{++}$ mediated pathway is involved in certain heart disease, the present invention provides the first evidence of MEF2 as a central mediator of the hypertrophic response. Essentially, the $Ca^{++}$-dependent protein calcineurin and CaMKIV can activate MEF2-dependent gene expression. Further it is demonstrated that the transcription activation domain of MEF2C is a nuclear target for hypertrophic signaling pathways.

Thus, in a particular embodiment of the present invention, there are provided methods for the treatment of cardiac hypertrophy. These methods exploit the inventors' observation, described in detail below, that MEF2 appears to up-regulate the expression of genes involved in the hypertrophic response. At its most basic, this embodiment will function by reducing the in vivo activity of MEF2 in individuals suspected of having undergone a hypertrophic response, currently undergoing a hypertrophic response, or in danger of cardiac hypertrophy. This may be accomplished by one of several different mechanisms. First, one may block the expression of the MEF2 protein. Second, one may directly block the function of the MEF2 protein by providing an agent that binds to or inactivates the MEF2 protein. And third, one may indirectly block the effect of MEF2 by interfering with one or more targets of MEF2.

The therapeutic compositions of the present invention may be administered in a manner similar to the administration of current treatments for heart conditions, such as aspirin, nitrates and beta blockers. Thus, the therapeutic formulations can be for oral administration in a tablet form to be swallowed (such as with aspirin) or to be dissolved under the tongue (such as with nitrates). These medicaments also can be provided as a patch to be worn on the skin, or as a topical cream to be applied to the skin.

a. Blocking Expression of MEF2

The most direct method for blocking MEF2 expression is via antisense technology. The term "antisense" is intended to refer to polynucleotide molecules complementary to a portion of a MEF2 RNA, or the DNA's corresponding thereto. "Complementary" polynucleotides are those which are capable of base-pairing according to the standard Watson-Crick complementary rules. That is, the larger purifies will base pair with the smaller pyrimidines to form combinations of guanine paired with cytosine (G:C) and adenine paired with either thymidine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo such as within a host animal, including a human subject.

Antisense constructs may be designed to bind to the promoter and other control regions, exons, introns or even exon-intron boundaries of a gene. It is contemplated that the most effective antisense constructs for the present invention will include regions complementary to the mRNA start site. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean polynucleotides that are substantially complementary over their entire length and have very few base mismatches. For example, sequences of fifteen bases in length may be termed complementary when they have a complementary nucleotide at thirteen or fourteen nucleotides out of fifteen. Naturally, sequences which are "completely complementary" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

The polynucleotides according to the present invention may encode an MEF2 gene or a portion of those genes that is sufficient to effect antisense inhibition of protein expression. The polynucleotides may be derived from genomic DNA, i.e., cloned directly from the genome of a particular organism. In other embodiments, however, the polynucleotides may be complementary DNA (cDNA). cDNA is DNA prepared using messenger RNA (mRNA) as template. Thus, a cDNA does not contain any interrupted coding sequences and usually contains almost exclusively the coding region(s) for the corresponding protein. In other embodiments, the antisense polynucleotide may be produced synthetically.

It may be advantageous to combine portions of the genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

It is contemplated that natural variants of exist that have different sequences than those disclosed herein. Thus, the present invention is not limited to use of the provided polynuclcotide sequence for MEF2 but, rather, includes use of any naturally-occurring variants. Depending on the particular sequence of such variants, they may provide additional advantages in terms of target selectivity, i.e., avoid unwanted antisense inhibition of related transcripts. The present invention also encompasses chemically synthesized mutants of these sequences.

As stated above, although the antisense sequences may be full length genomic or cDNA copies, or large fragments thereof, they also may be shorter fragments, or "oligonucleotides," defined herein as polynucleotides of 50 or less bases. Although shorter oligomers (8–20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45 or 50 base pairs will be used. While all or part of the gene sequence may be employed in the context of antisense construction, statistically, any sequence of 17 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression.

As an alternative to targeted antisense delivery, targeted ribozymes may be used. The term "ribozyme" is refers to an RNA-based enzyme capable of targeting and cleaving particular base sequences in both DNA and RNA. Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense polynucleotide. Ribozyme sequences also may be modified in much the same way as described for antisense polynucleotide. For example, one could incorporate non-Watson-Crick bases, or make mixed RNA/DNA oligonucleotides, or modify the phosphodiester backbone, or modify the 2'-hydroxy in the ribose sugar group of the RNA.

Alternatively, the antisense oligo- and polynucleotides according to the present invention may be provided as RNA via transcription from expression constructs that carry nucleic acids encoding the oligo- or polynucleotides. Throughout this application, the term "expression construct" is meant to include any type of genetic construct containing a nucleic acid encoding an antisense product in which part or all of the nucleic acid sequence is capable of being transcribed. Typical expression vectors include bacterial plasmids or phage, such as any of the pUC or Bluescript™ plasmid series or, as discussed further below, viral vectors adapted for use in eukaryotic cells.

In preferred embodiments, the nucleic acid encodes an antisense oligo- or polynucleotide is placed in a replicable cloning vehicle that supports expression of the antisense molecule with cis-acting transcriptional and translational signals. The expression constructs will comprise the gene in question and various regulatory elements as described herein below.

b. Blocking Function of MEF2

In another embodiment, it may be desirable to block the function of an MEF2 polypeptide rather than inhibit its expression. This can be accomplished by use of organochemical compositions that interfere with the function of MEF2, by use of an antibody that blocks an active site or binding site on MEF2, or by use of a molecule that mimics an MEF2 target. With respect to organochemical inhibitors, such compounds may be identified in standard screening assays. Once identified, such an inhibitor may be used to inhibit MEF2 function in a therapeutic context.

The methods by which antibodies are generated are well known to those of skill in the art, and are detailed elsewhere in the specification. Again, antibodies that bind MEF2 may be screened for other functional attributes.

A particularly useful antibody for blocking the action of MEF2 is a single chain antibody. Methods for the production of single-chain antibodies are well known to those of skill in the art. The skilled artisan is referred to U.S. Pat. No. 5,359,046, (incorporated herein by reference) for such methods. A single chain antibody, preferred for the present invention, is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990, Chaudhary et al., 1990). These Fvs lack the constant regions (Fc) present in the heavy and light chains of the native antibody.

With respect to inhibitors that mimic MEF2 targets, the use of mimetics provides one example of custom designed molecules. Such molecules may be small molecule inhibitors that specifically inhibit MEF2 protein activity. Such molecules may be sterically similar to the actual target compounds, at least in key portions of the target's structure and or organochemical in structure. Alternatively these inhibitors may be peptidyl compounds, these are called peptidomimetics. Peptide mimetics are peptide-containing molecules which mimic elements of protein secondary structure. See, for example, Johnson et al. (1993). The underlying rationale behind the use of peptide mimetics is that the peptide backbone of proteins exists chiefly to orient amino acid side chains in such a way as to facilitate molecular interactions, such as those of ligand and receptor. An exemplary peptide mimetic of the present invention would, when administered to a subject, bind to MEF2.

Successful applications of the peptide mimetic concept have thus far focused on mimetics of β-turns within proteins, which are known to be highly antigenic. Likely β-turn structures within an antigen of the invention can be predicted by computer-based algorithms as discussed above. Once the component amino acids of the turn are determined, mimetics can be constructed to achieve a similar spatial orientation of the essential elements of the amino acid side chains, as discussed in Johnson et al., (1993).

c. Blocking of a MEF2 Target

As discussed above, one of the benefits of the present invention is the identification of targets upon which MEF2 acts. These targets may be binding partners such as calcineurin and GATA4 or other genes that are upregulated by an activated MEF2 interaction with GATA4, such as α-skeletal actin, β-MHC, ANF, BNP. In order to prevent MEF2 from interacting with these targets, one may take a variety of different approaches. For example, one may generate antibodies against the target and then provide the antibodies to the subject in question, thereby blocking access of MEF2 to the target molecule.

In yet another embodiment, antisense methodologies may be employed in order to inhibit the interaction of MEF2 with its target, seeing as the MEF2 binding partner is a DNA molecule. Alternatively, one may design a polypeptide or peptide mimetic that is capable of interacting with the MFE2 target in the same fashion as MEF2, but without any MEF2-like effect on the target.

In a preferred embodiment, the present invention will provide an agent that binds competitively to GATA4. In a more preferred embodiment, the agent will have an even greater affinity for the GATA4 than does MEF2 does. Affinity for the GATA4 can be determined in vitro by performing kinetic studies on binding rates.

Other compounds may be developed based on computer modeling and predicted higher order structure, both of the MEF2 molecule and of the identified target molecules. This approach has proved successful in developing inhibitors for a number of receptor-ligand interactions.

6. Genetic Constructs and Gene Transfer

In particular aspects of the present invention, it may be desirable to place a variety of cardiac genes into expression constructs and monitor their expression. For example, a cardiac hypertrophy gene such as BNP, MHC and the like may be tested by introducing into cultured cardiomyocytes an expression construct comprising a promoter operably linked to a hypertrophy-sensitive gene or genes and monitoring the expression of the hypertrophy-sensitive gene or genes. Expression constructs are also used in generating transgenic animals include a promoter for expression of the construct in an animal cell and a region encoding a gene product which modulates transcription of at least one gene that is expressed in cardiomyocytes in response to a hypertrophic signal. In other embodiments, the expression construct encodes an antisense oligo- or polynucleotide is placed in a replicable cloning vehicle that supports expression of the antisense molecule for the therapeutic purposes discussed above.

a. Genetic Constructs

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

i. Cardiomyocyte Specific Regulatory Elements

Transcriptional regulatory elements which are suitable for use in the present invention include which direct the transcription of a coding region to which they are operably linked preferentially in cardiomyocytes. By "preferentially" is meant that the expression of the transgene in cardiomyocytes is at least about 10-fold, more preferably at least about 10-fold to about 50-fold, even more preferably at least about 50-fold to 100-fold, even more preferably more than 100-fold greater than that in non-cardiomyocytes. Preferably, expression of the transgene is below detectable limits in cells other than cardiomyocytes, as indicated by reporter gene assays well known to those of skill in the art.

ii. General Promoters

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the *Rous sarcoma* virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitro, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992, Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of $E.$ $coli.$ The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycydline activates transcription. For gene transfer vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene transfer vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues.

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

iii. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

iv. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

b. Gene Transfer

There are a number of ways in which expression vectors may introduced into cells. In certain embodiments of the invention, the expression construct comprises a virus or engineered construct derived from a viral genome. In other embodiments, non-viral delivery is contemplated. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). Delivery mechanisms are discussed in further detail herein below.

i. Non-viral transfer

The present section provides a discussion of methods and compositions of non-viral gene transfer. DNA constructs of the present invention are generally delivered to a cell, and in certain situations, the nucleic acid or the protein to be transferred may be transferred using, non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAF-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the particular gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In another particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene delivery.

Liposome-mediated nucleic acid delivery and expression of foreign DNA in vitiro has been very successful. Using the β-lactamase gene, Wong et al. (1980) demonstrated the feasibility of liposome-mediated delivery and expression of forein DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In certain embodiments, gene transfer may more easily be performed under ex vivo conditions. Ex vivo gene application refers to the isolation of cells from an animal, the delivery of a nucleic acid into the cells in vitro, and then the return of the modified cells back into an animal. This may involve the surgical removal of tissue/organs from an animal or the primary culture of cells and tissues.

ii. Viral Transfer

Adenovirus. One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide, a protein, a polynucleotide (e.g., ribozyme, or an mRNA) that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreigyn sequences up to 7 kb (Grunhaus and Horwitz, 1992). In contrast to retroviruses, the adenoviral infection of host cells does not result in chromosomal integration because adenoviral DNA can replicate in an episomal manner without potential genotoxicity. As used herein, the term "genotoxicity" refers to permanent inheritable host cell genetic alteration. Also, adenoviruses are structurally stable, and no genome rearrangement has been detected after extensive amplification of normal derivatives. Adenovirus can infect virtually all epithelial cells regardless of their cell cycle stage. So far, adenoviral infection appears to be linked only to mild disease such as acute respiratory disease in non-immunosuppressed humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

The E3 region encodes proteins that appears to be necessary for efficient lysis of Ad infected cells as well as preventing TNF-mediated cytolysis and CTL mediated lysis of infected cells. In general, the E4 region encodes is believed to encode seven proteins, some of which activate the E2 promoter. It has been shown to block host mRNA transport and enhance transport of viral RNA to cytoplasm. Further the E4 product is in part responsible for the decrease in early gene expression seen late in infection. E4 also inhibits E1A and E4 (but not E1B) expression during lytic growth. Some E4 proteins are necessary for efficient DNA replication however the mechanism for this involvement is unknown. E4 is also involved in post-transcriptional events in viral late gene expression; i.e., alternative splicing of the tripartite leader in lytic growth. Nevertheless, E4 functions are not absolutely required for DNA replication but their lack will delay replication. Other functions include negative regulation of viral DNA synthesis, induction of sub-nuclear reorganization normally seen during adenovirus infection, and other functions that are necessary for viral replication, late viral mRNA accumulation, and host cell transcriptional shut off.

In a current system, recombinant adenovirus is generated from homologous recombination between shuttle vector and provirus vector. Possible recombination between the proviral vector and Ad sequences in 293 cells, or in the case of pJM17 plasmid spontaneous deletion of the inserted pBR322 sequences, may generate full length wild-type Ad5 adenovirus. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993; Shenk, 1978).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclose improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking is initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known scrotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical, medical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression investigations (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene transfer (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993), intranasal inoculation (Ginsberg et al., 1991), aerosol administration to lung (Bellon, 1996) intraperitoneal administration (Song et al., 1997), Intra-pleural injection (Elshami et al., 1996) administration to the bladder using intravesicular administration (Werthman, et al., 1996), Subcutaneous injection including intraperitoneal, intrapleural, intramuscular or subcutaneously) (Ogawa, 1989) ventricular injection into myocardium (heart, French et al., 1994), liver perfusion (hepatic artery or portal vein, Shiraishi et al., 1997) and stereotactic inoculation into the brain (Le Gal La Salle et al., 1993).

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Herpesvirus. Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene transfer vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1995). The expression of α genes, the first set of genes to be expressed after infection, is enhanced by the virion protein number 16, or α-transducing factor (Post et al., 1981, Batterson and Roizman, 1983). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene transfer contexts (U.S. Pat. No. 5,672,344).

Adeno-Associated Virus. Recently, adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associated with the latter, AAV has not been associated with any such pathological indications.

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin and Berns, 1989; Kotin et al., 1990; Kotin et al., 1991; Samulski et al., 1991); and AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Berns, 1990; Berns and Bohensky, 1987; Bertran et al., 1996; Kearns et al., 1996; Ponnazhagan et al., 1997a). Until recently, AAV was believed to infect almost all cell types, and even cross species barriers. However, it now has been determined that AAV infection is receptor-mediated (Ponnazhagan et al., 1996; Mizukami et al., 1996).

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by Srivastava et al. (1983), and in U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

Vaccinia Virus. Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

c. Selection Methods

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenlous protein normally synthesized by the cell in question.

Examples of useful mammalian host cell lines are Vero and HeLa cells and cell lines of Chinese hamster ovary, W138, BHK, COS-7, 293, HepG2. NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., a cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

Thus, following introduction of the expression construct into the cells, expression of the reporter gene can be determined by conventional means. Any assay which detects a product of the reporter gene, either by directly detecting the protein encoded by the reporter gene or by detecting an enzymatic product of a reporter gene-encoded enzyme, is suitable for use in the present invention. Assays include colorimetric, fluorimetric, or luminescent assays or even, in the case of protein tags, radioimmunoassays or other immunological assays. Transfection efficiency can be monitored by co-transfecting an expression construct comprising a constitutively active promoter operably linked to a reporter gene.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

7. Monitoring Transgene Expression

In order to determine whether the MEF2 indicator construct has been successfully incorporated into the genome of the transgenic animal, a variety of different assays may be performed. Transgenic animals can be identified by analyzing their DNA. For this purpose, when the transgenic animal is a rodent, tail samples (1 to 2 cm) can be removed from three week old animals. DNA from these or other samples can then be prepared and analyzed by Southern blot, PCR, or slot blot to detect transgenic founder ($F_0$) animals and their progeny ($F_1$ and $F_2$).

a. Pathological studies

The various F0, F1 and F2 animals that carry a transgene can be analyzed by any of a variety of techniques, including immunohistology, electron microscopy, electrocardiography and making determinations of total and regional heart weights, measuring cardiomyocyte cross-sectional areas and determining numbers of cardiomyocytes. Immunohistological analysis for the expression of a transgene by using an antibody of appropriate specificity can be performed using known methods. Morphometric analyses to determine regional weights, cardiomyocyte cross-sectional areas and numbers of cardiomyocyte nuclei can be performed using known methods. Hearts can be analyzed for function, histology and expression of fetal cardiac genes.

In immuno-based analyses, it may be necessary to rely on indicator binding antibodies. A general review of antibody production techniques is provided. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

The immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and tittering is repeated until a suitable titer is achieved. When a desired level of immunogenicity is obtained, the immunized animal can be bled and the serum isolated and stored, and/or the animal can be used to generate mAbs.

A polyclonal antibody is prepared by immunizing an animal with an immunogen comprising an MEF2 polypeptide, or fragment thereof, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit may be a preferred choice for production of polyclonal antibodies.

To obtain monoclonal antibodies, one would also immunize an experimental animal, an antigenic composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired target peptide.

It is proposed that the monoclonal antibodies of the present invention also will find useful application in standard immunochemical procedures, such as ELISA and Western blot methods, as well as other procedures which may utilize antibody specific to MEF2 epitopes. Additionally, it is proposed that monoclonal antibodies specific to MEF2 may be utilized in other useful applications. For example, an anti-idiotype antibody to an anti-MEF2 antibody may well mimic an MEF2 binding site, thus providing a tool for the identification of MEF2 targets.

b. Analysis of Transgene Expression by Measuring mRNA Levels

Messenger RNA can be isolated by any method known in the art, including, but not limited to, the acid guanidinium thiocyanate-phenol:chloroform extraction method (Chomczynski and Sacchi 1987), from cell lines and tissues of transgenic animals to determine expression levels by Northern blots, RNAse and nuclease protection assays.

c. Analysis of Transgene Expression by Measuring Protein Levels

Protein levels can be measured by any means known in the art, including, but not limited to, western blot analysis, ELISA and radioimmunoassay, using one or more antibodies specific for the protein encoded by the transgene.

For Western blot analysis, protein fractions can be isolated from tissue homogenates and cell lysates and subjected to Western blot analysis as described by, for example, Harlow et al., *Antibodies: A Laboratory Manual,* (Cold Spring Harbor, N.Y., 1988);, Brown et al., (1983); and Tate-Ostroff et. al. (1989).

For example, the protein fractions can be denatured in Laemmli sample buffer and electrophoresed on SDS-Polyacrylamide gels. The proteins are then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of the transgene-encoded proteins.

ELISAs are preferably used in conjunction with the invention. For example, an ELISA assay may be performed where target protein from a sample is immobilized onto a selected surface, preferably a surface exhibiting a protein affinity such as the wells of a polystyrene microtiter plate. The plate is washed to remove incompletely adsorbed material and the plate is coated with a non-specific protein that is known to be antigenically neutral with regard to the test antibody, such as bovine serum albumin (BSA), casein or solutions of powdered milk. This allows for blocking of nonspecific adsorption sites on the immobilizing surface and thus reduces the background caused by nonspecific binding of antisera onto the surface.

Next, the antibody is added to the plate in a manner conducive to immune complex (antigen/antibody) formation. Such conditions preferably include diluting the antisera/antibody with diluents such as BSA, bovine gamma globulin (BGG) and phosphate buffered saline (PBS)/Tween®. These added agents also tend to assist in the reduction of nonspecific background. The plate is then allowed to incubate for from about 2 to about 4 hr. at temperatures preferably on the order of about 25° to about 27° C. Following incubation, the plate is washed so as to remove non-immunocomplexed material. A preferred washing procedure includes washing with a solution such as PBS/Tween®, or borate buffer.

Following formation of specific immunocomplexes between the sample and antibody, and subsequent washing, the occurrence and amount of immunocomplex formation may be determined by subjecting the plate to a second antibody probe, the second antibody having specificity for the first (usually the Fc portion of the first is the target). To provide a detecting means, the second antibody will preferably have an associated enzyme that will generate a color development upon incubating with an appropriate chromogenic substrate. Thus, for example, one will desire to contact and incubate the antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generations e.g., using a visible spectrum spectrophotometer. Variations on this assay, as well as completely different assays (radioimmunprecipitation, immunoaffinity chromatograph, Western blot) also are contemplated as part of the present invention.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analyses.

Other immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

8. Screening for Modulators of Cardiac Hypertrophy

The present invention also contemplates the screening of compounds for their ability to inhibit cardiac hypertrophy. The ability of the present inventors to create cellular, organ and organismal systems which mimic this disease provide an ideal setting in which to test various compounds for therapeutic activity. Particularly preferred compounds will be those useful in inhibiting cardiac hypertrophy and preventing or reversing heart disease. In the screening assays of the present invention, the candidate substance may first be screened for basic biochemical activity—e.g., binding, to a target molecule—and then tested for its ability to inhibit a hypertrophic phenotype, at the cellular, tissue or whole animal level.

a. Inhibitors and Assay Formats
i. Assay Formations

The present invention provides methods of screening for inhibitors of cardiac hypertrophy. It is contemplated that this screening techniques will prove useful in the identification of compounds that will block cardiac hypertrophy and/or reduce cardiac hypertrophy once developed.

In these embodiments, the present invention is directed to a method for determining the ability of a candidate substance to inhibit hypertrophy, generally including the steps of:

(a) providing a cardiomyocyte that contains an indicator gene under the control of MEF2 inducible regulatory sequences that exhibits a hypertrophic phenotype;

(b) contacting said cell with a candidate inhibitor; and (c) monitoring said cell for an effect on indicator gene expression as compared to a similar cell not treated with said candidate inhibitor.

In one aspect, the cells express an indicator gene under the control of various regulatory elements including the transcriptional regulatory elements (TRE) from BZLF1 and desmin gene. These elements are regulated by MEF2 and provide a measure, through expression of the controlled indicator gene, of MEF2 transcriptional activator activity. Any regulatory element subject to MEF2 control may be utilized and, as illustrated by the examples below, it may be useful to provide one or more repeats of a TRE that is affected by MEF2. Indicator genes include lacZ, GFP luciferase, and other similar markers.

In preferred aspects, the cells express lacZ under the control of three tandem copies of MEF2 binding sites. In certain embodiments, the other genes involved in the MEF2 pathway may be altered to achieve the same effect.

ii. Inhibitors and Activators of MEF2

An inhibitor according to the present invention may be one which exerts its inhibitory effect upstream or downstream of MEF2, or on MEF2 directly. Regardless of the type of inhibitor identified by the present screening methods, the effect of the inhibition by such a compound results in inhibition of the cardiac hypertrophy, or some related biochemical or physiologic aspect thereof, for example, growth, $Ca^{++}$-dependent gene expression and the like in the absence of the added candidate substance.

iii. Candidate Substances

As used herein the term "candidate substance" refers to any molecule that may potentially inhibit cardiac hypertrophy. The candidate substance may be a protein or fragment thereof, a small molecule inhibitor, or even a nucleic acid molecule. It may prove to be the case that the most useful pharmacological compounds will be compounds that are structurally related to other known modulators of hypertrophy, such as cyclosporin A and FK506. Such an endeavor often is know as "rational drug design," and includes not only comparisons with know inhibitors, but predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like MEF2, or a fragment thereof, thereby creating a competitive inhibitor of MEF2. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of hypertrophic response.

Other suitable inhibitors include antisense molecules, ribozymes, and antibodies (including single chain antibodies), each of which would be specific for a target located within the MEF2 pathway. Such compounds are described in greater detail elsewhere in this document. For example, an antisense molecule that bound to a translational or transcriptional start site of MEF2, or an antibody that bound to MEF2, would be ideal candidate inhibitors.

"Effective amounts" in certain circumstances are those amounts effective to reproducibly decrease hypertrophy from the cell in comparison to their normal levels. Compounds that achieve significant appropriate changes in activity will be used.

Significant changes in cardiac hypertrophy, e.g., as measured using cardiomyocyte growth, $Ca^{++}$ response, cardiac gene expression, and the like are represented by a decrease in activity of at least about 30%–40%, and most preferably, by changes of at least about 50%, with higher values of course being possible. The active compounds of the present invention also may be used for the generation of antibodies which may then be used in analytical and preparatory techniques for detecting and quantifying further such inhibitors.

It will, of course, be understood that all the screening methods of the present invention are useful in themselves notwithstanding the fact that effective candidates may not be found. The invention provides methods for screening for such candidates, not solely methods of finding them.

b. In vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to the MEF2 molecule or fragment thereof is provided.

The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as MEF2). Competitive binding assays can be performed in which one of the agents (MEF2 for example) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, MEF2 and washed. Bound polypeptide is detected by various methods.

Purified target, such as MEF2, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region (e.g., the C-terminus of MEF2) to a solid phase.

c. In cyto Assays

Various cell lines that exhibit cardiac hypertrophic characteristics can be utilized for screening of candidate substances. For example, cells containing engineered indicators, as discussed above, can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (growth, size. $Ca^{++}$ effects). Alternatively, molecular analysis may be performed in which the function of MEF2 and related pathways may be explored. This involves assays such as those for protein expression, enzyme function, substrate utilization, mRNA expression (including differential display of whole cell or polyA RNA) and others.

d. In vivo Assays

The present invention particularly contemplates the use of various animal models. Here, transgenic mice have been created with constructs that permit MEF2 activity to be easily monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

Determining the effectiveness of a compound in vivo involves examining the expression of the indicator gene.

9. Pharmaceutical Compositions

Where clinical application of an active ingredient (drugs, polypeptides, antibodies or liposomes containing antisense oligo- or polynucleotides or expression vectors) is undertaken, it will be necessary to prepare a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the active ingredient, as discussed above, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. A preferred embodiment delivery route, for the treatment of a disseminated disease state is systemic, however, regional delivery is also contemplated.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration the intended goal of treatment and the potency, stability and toxicity of the particular therapeutic substance.

10. Looking for Downstream Genes

The identification of genes downstream of MEF2 knockout mice also are contemplated in the present invention. These genes can be identified by comparing differentially expressed genes of the MEF2 knockout mice to those of normal mice. In a preferred embodiment, this will be accomplished by "differential display" as discussed below.

RNA fingerprinting is a means by which RNAs isolated from many different tissues cell types or treatment groups may be sampled simultaneously to identify RNAs whose relative abundances vary. Two forms of this technology were developed simultaneously and reported in 1992 as RNA fingerprinting and differential display (Liang and Pardee, 1992; Welsh et al., 1992). (See also Liang & Pardee, U.S. Pat. Nos. 5,262,311, 5,665,547 incorporated herein by reference in its entirety.) Both techniques were utilized in the studies described below. Some of the studies described herein were performed similarly to Donahue et al., 1994.

All forms of RNA fingerprinting by PCR are theoretically similar but differ in their primer design and application. The most striking difference between differential display and other methods of RNA fingerprinting is that differential display utilizes anchoring primers that hybridize to the polyA tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchored primer composed of oligo-dT. The oligo-dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis with ethidium bromide staining or autoradiography. A side by side comparison of fingerprints from different cell derived RNAs using the same oligonucleotide primers identifies mRNAs that are differentially expressed.

Differential display technology has been demonstrated as being effective in identifying genes that are differentially expressed in cancer (Liang & Pardee, 1992; Wong et al., 1993; Sager et al., 1993; Mok et al., 1994; Watson et al., 1994; Chen et al., 1995; An et al., 1995). The present invention utilizes the RNA fingerprinting technique to identify genes that are differentially expressed in prostate cancer. These studies utilized RNAs isolated from tumor tissues and tumor-derived cell lines that behave as tumors cells with different metastatic potential.

The underlying concept of these studies was that genes that are differentially expressed in cells with different metastatic potentials may be used as indicators of metastatic potential. Since metastasis is a prerequisite for prostate cancer progression to life threatening pathologies, indicators of metastatic potential are likely to be indicators of pathological potential.

Cells often are harvested in late log phase of growth. RNA may be isolated by the guanidinium thiocyanate method (Chomczynski & Sacchi, 1987). After RNA isolation, the nucleic acids are precipitated with ethanol. The precipitates are pelleted by centrifugation and redissolved in water. The redissolved nucleic acids are then digested with RNase-free DNase I (Boehringer Mannheim, Inc.) following the manufacturer's instructions, followed by organic extraction with phenol:chloroform:isoamylalcohol (25:24:1) and reprecipitation with ethanol.

The DNase I treated RNA is then pelleted by centrifugation and redissolved in water. The purity and concentration of the RNA in solution is estimated by determining optical density at wave lengths of 260 nm and 280 nm (Sambrook et al., 1989). A small aliquot of the RNA is separated by gel electrophoresis in a 3% formaldehyde gel with MOPS buffer (Sambrook et al., 1989) to confirm the estimation of concentration and to determine if the ribosomal RNAs were intact. This RNA is referred to as total cell RNA.

There were two kinds of RNA fingerprinting studies performed with the total cell RNA. The first of these kinds of studies follow the differential display protocol of Liang and Pardee (1992) except that they are modified by using 5' biotinylated primers for nonisotopic PCR product detection.

In these studies, 0.2 µg of total cell RNA are primed for reverse transcription with an anchoring primer according to the present invention, then two arbitrarily chosen nucleotides, including all of the possible combinations of each nucleotide at these positions. Reverse transcription is performed with 200 units of MMLV (Moloney Murine Leukemia Virus) reverse transcriptase (GIBCO/BRL) in the presence of 50 mM Tris-HCl (pH 8.3), 75 mM KCl, 3 mM $MgCl_2$, 10 mM DTT, 500 µM dNTP, 1 µM anchored primer and 1 U/µl RNase inhibitor. The reaction mixture is incubated at room temperature for 10 minutes, then at 37° C. for 50 minutes. After reverse transcription the enzyme is inactivated by heating to 65° C. for 10 minutes.

One tenth of the resulting reverse transcription reactions is then amplified by PCR using the same anchoring primer as used in the reverse transcription step and a second oligonucleotide of arbitrarily chosen sequences. The PCR reaction contains 10 mM Tris-HCl (pH 8.3), 50 mM KCl, 20 µM dNTP, 1.5 µM $MgCl_2$, 200 nM arbitrary decamer, 1 µM anchored primer, and 1 unit of Taq DNA polymerase (Bochringer Mannheim) in a 40 µl volume. The amplification is performed in a thermal cycler (MJ Research) for 30 cycles with denaturing at 94° C. for 30 sec, annealing at 40° C. for 2 min, and extending at 72° C. for 30 sec, $^{35}$S-dATP is added in the PCR reaction.

The PCR products are then separated on a 6% TBF-urea sequencing gel (Sambrook et al., 1989) and detected by autoradiography. Differentially appearing PCR products may be excised from the gels, reamplified using the same primers used in the original amplification, and cloned using the TA cloning strategy (Invitrogen, Inc. and Promega, Inc.).

The second type of RNA fingerprinting studies more closely resembled the protocol of Welsh et al. (1992). This approach uses a variation of the above as modified by the use of agarose gels and non-isotopic detection of bands by ethidium bromide staining (An et al., 1995). Total RNAs are isolated from the frozen prostate tissues or cultured cells as described (Chomczynski & Sacchi, 1987). Ten micrograms of total cellular RNAs are treated with 5 units of RNAse-free DNAse I (GIBCO/BRL) in 20 mM Tris-HCl (pH 8.4), 50 mM KCl, 2 mM $MgCl_2$, and 20 units of RNAse inhibitor (Boehringer Mannheim). After extraction with phenol/chloroform and ethanol precipitation, the RNAs are redissolved in DEPC-treated water.

Two µg of each total cell RNA sample are reverse transcribed into cDNA using randomly selected hexamer primers and MMLV reverse transcriptase (GIBCO/BRL).

PCR was performed using one or two arbitrarily chosen oligonucleotide primers (10–12 mers). PCR conditions are: 10 mM Tris-HCl (pH 8.3), 50 mM KCl, 1.5 mM $MgCl_2$, 50 µM dNTPs, 0.2 µM of primer(s), 1 unit of Taq DNA polymerase (GIBCO/BRL) in a final volume of 20 µl. The amplification parameters include 35 cycles of reaction with 30 sec denaturing at 94° C., 90 sec annealing at 40° C., and αsec extension at 72° C. A final extension at 72° C. is performed for 15 min. The resulting PCR products are resolved into a fingerprint by size separation by electrophoresis through 2% agarose gels in TBE buffer (Sambrook et al., 1989). The fingerprints are visualized by staining with ethidium bromide. No reamplification is performed.

Differentially appearing PCR products, that might represent differentially expressed genes, are excised from the gel with a razor blade, purified from the agarose using, the Geneclean kit (Bio 101, Inc.), eluted in water and cloned directly into plasmid vectors using the TA cloning strategy (Invitrogen, Inc., and Promega, Inc.). These products are not reamplified after the initial PCR fingerprinting protocol.

11. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Preparation of primary rat cardiomyocytes. Cardiomyocyte cultures are prepared by dissociation of 1-day old neonatal rat hearts and were differentially plated to remove fibroblasts. To induce the hypertrophic response, AngII and PE are added to cardiomyocyte cultures at 10 nM and 10 µM, respectively, in serum-free M199 media. The culture media containing either agonist is changed every 12 hours for a period of 72 hours.

Immunocytochemistry. To visualize sarcomeric organization in primary cardiomyocytes, anti-a-actinin mouse monoclonal antibody is used (Sigma). Cells are washed in 1× PBS, fixed in 3.7% paraformaldehyde for 5 minutes, washed three times with 1× PBS and then pre-blocked in 1× PBS containing 2% horse serum, 2% BSA, and 0.1% NP40 for 30 minutes. Anti-a-actinin antibody is added at a dilution of 1:800 in flesh pre-block solution and incubated for an additional 30 minutes. Subsequently, cells are washed three times in 1× PBS with 0.1% NP40. Anti-mouse TRITC-conjugated secondary antibody is then added at a dilution of 1:400 for 30 minutes in pre-block solution and the cells are agaiin washed three times in 1× PBS containing 0.1% NP40. Nuclear staining for DNA is performed with 0.5 µg/ml of bis-benzimide in PBS for 15 min followed by three rinses with PBS.

RNA analysis. Total RNA was collected and purified with Triazol reagent (Gibco BRL) as recommended. RNA from wild-type and transgenic hearts, as well as from cultured cardiomyocytes, was subjected to dot blot hybridization against a panel of oligonucleotide probes as described previously (Jones et al., 1996).

Histology. Hearts from wild-type and transgenic mice were subjected to histological analysis. Briefly, hearts were collected, fixed overnight in 10% formalin buffered with PBS, dehydrated in ethanol, transferred to xlyene then into paraffin. Paraffin-embedded hearts were sectioned at 4 µM and subsequently stained with hematoxylin and eosin for routine histologic examination or with Masson trichrome for collagen (Woods and Ellis, 1994).

Example 2

The Role of MEF2 in Cardiac Gene Expression

Structure-function studies. There are four vertebrate MEF2 genes, whose products are schematized in FIG. 1. Through extensive mutational analyses, the functional domains of the MEF2 proteins have been characterized (Molkentin et al., 1995; Martin et al., 1993; Molkentin et al., 1996a; 1996b). These studies demonstrate that the N-terminal MADS-box mediates DNA binding and dimerization. The adjacent MEF2 domain influences DNA binding affinity and interactions with myogenic bHLH proteins, and the C-terminal regions of the MEF2 factors contain multiple independent transcriptional activation domains.

Cooperative activation of muscle transcription by MEF2 and myogenic bHLH factors. In the skeletal muscle lineage, MEF2 acts combinatorially with members of the MyoD family of bHLH transcription factors to activate muscle gene transcription. It has been demonstrated that the MADS-box of the MEF2 proteins interacts directly with the bHLH regions of the myogenic factors (Molkentin et al., 1995). This biochemical model for combinatorial control of muscle gene expression by MEF2 factors is supported by genetic studies in Drosophila, which have shown that MEF2 is an essential cofactor for differentiation of all types of myoblasts, skeletal, cardiac and visceral (Lilly et al., 1995; Bour et al., 1995).

Figure 3:
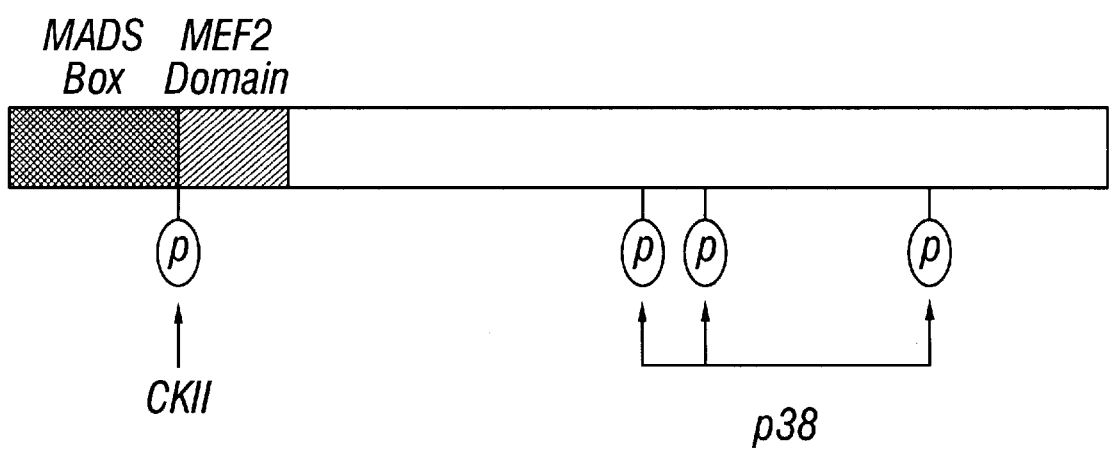
FIG. 3. Locations of known phosphorylation sites in MEF2C.

MEF2 phosphorylation. Phosphopeptide mapping studies demonstrate that MEF2 factors contain multiple phosphorylation sites. It is shown that a casein kinase-II (CKII) site in the MADS-box enhances the affinity of MEF2C for DNA (Molkentin et al., 1996c). This site is conserved in all known MEF2 proteins in organisms ranging from Drosophila and C. elegans to humans, consistent with its importance for MEF2 function. It has not yet been determined whether this site is subject to regulated phosphorylation. A schematic diagram of MEF2C and the phosphorylation sites that have been defined to date are shown in FIG. 3.

Also it is shown that the transcriptional activity of MEF2C is dramatically enhanced in the presence of activated PKC. Transfection of fibroblasts with a MEF2-dependent reporter gene, along with expression vectors for MEF2C and an activated form of PKC, results in a greater than 10-fold increase in transcriptional activity with no apparent increase in DNA binding. These results suggest that may MEF2C mediate certain transcriptional effects of PKC.

MEF2 gene knockouts. By gene targeting, the four MEF2 genes in ES cells and transgenic mice are inactivated. Mice lacking MEF2C die at E9.5 from severe cardiovascular defects that include the absence of a right ventricle and the failure of the vascular system to form (Lin et al., 1997). In addition, a subset of cardiac contractile protein genes, including a-MHC a-cardiac actin and ANF, fail to be expressed in the developing heart. In contrast, several other cardiac genes, such as myosin light chains 2A and −2V, are expressed at normal levels in the hearts of MEF2C mutant embryos, indicating that they were MEF2C-independent.

Since these genes also contain essential MEF2 binding sites in their promoters, it is likely that another member of the MEF2 family can support their expression in the absence of MEF2C. MEF2B is coexpressed with MEF2C in the early heart and is upregulated in MEF2C mutant embryos, making it a likely candidate for playing a partially overlapping role with MEF2C. The finding that a subset of cardiac genes is dependent on MEF2C indicates that muscle genes can discriminate between different members of the MEF2 family.

Example 3

Induction of MEF2 Activity in vitro by Hypertrophic Signaling

Figure 4:
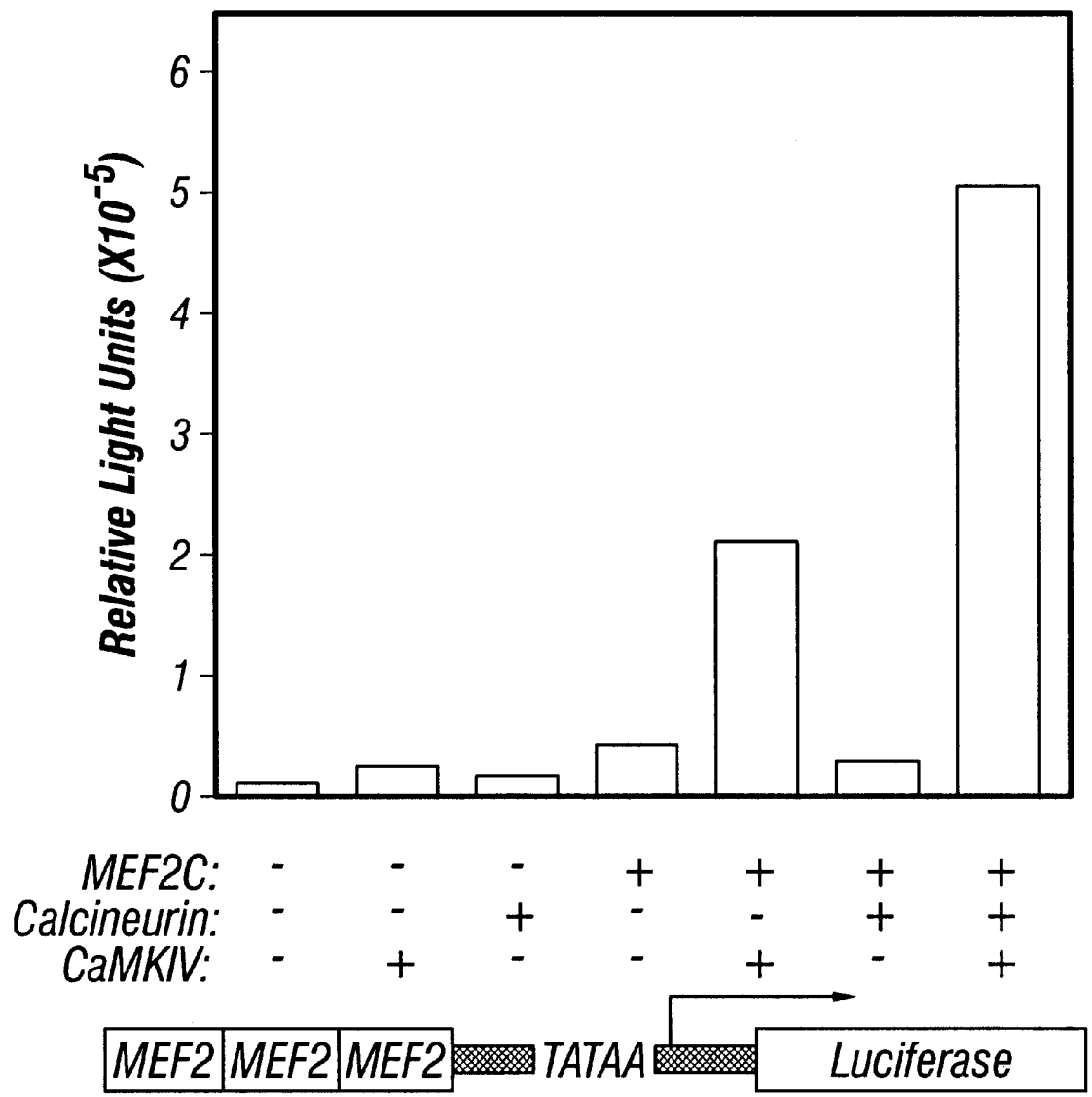
FIG. 4. CaMKIV and calcineurin synergize to activate a MEF2-dependent reporter gene.
Figure 5:
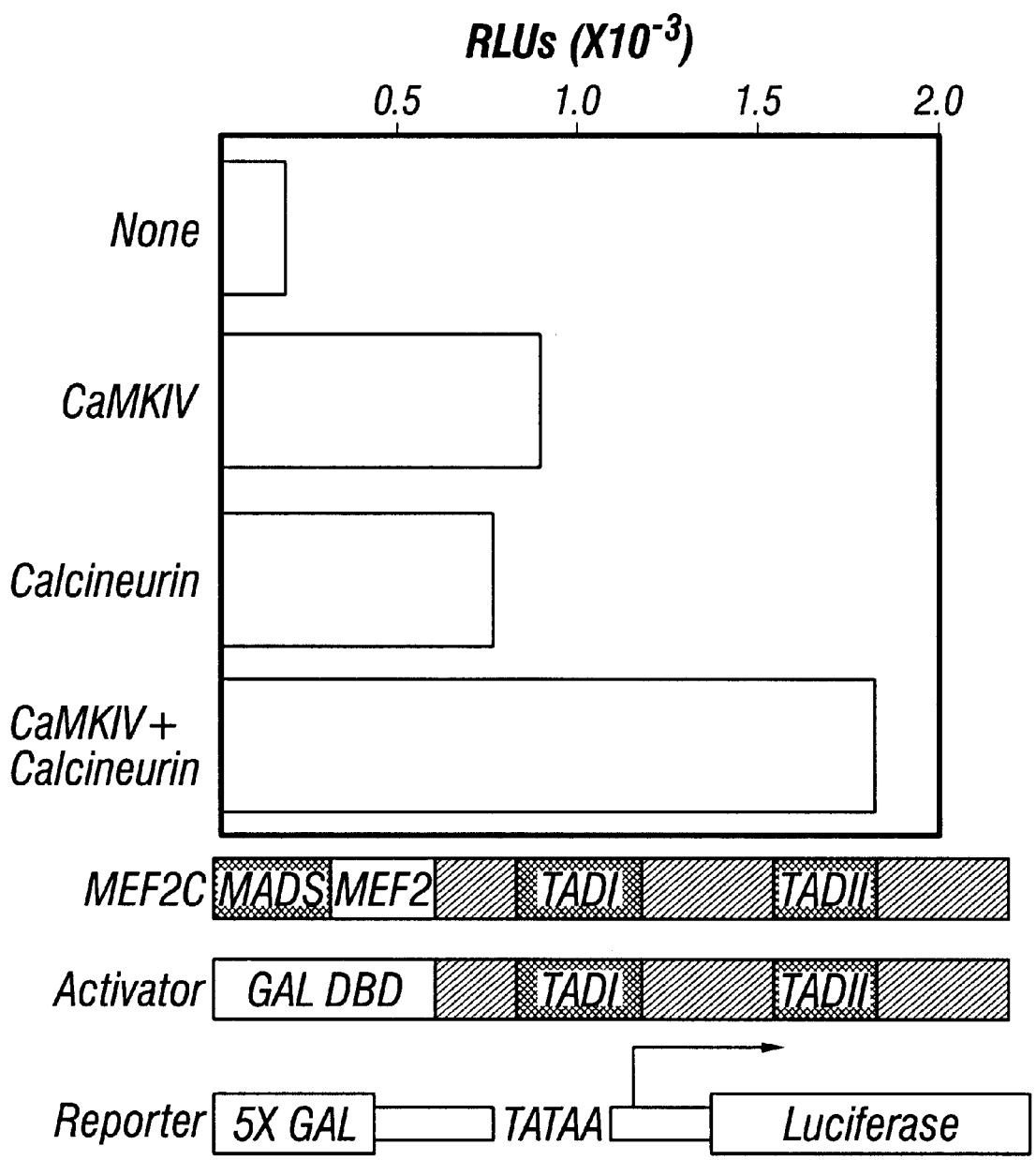
FIG. 5. CaMKIV and calcineurin synergize to activate a GAL4-dependent reporter gene in the presence of a GAL4-MEF2C fusion protein. Cardiomyocytes were transiently transfected with a GAL4-MEF2C fusion gene, as shown, and a GAL4-dependent reporter gene. The transcriptional activity of MEF2C was dramatically enhanced by CaMKIV and calcineurin.
Figure 6:
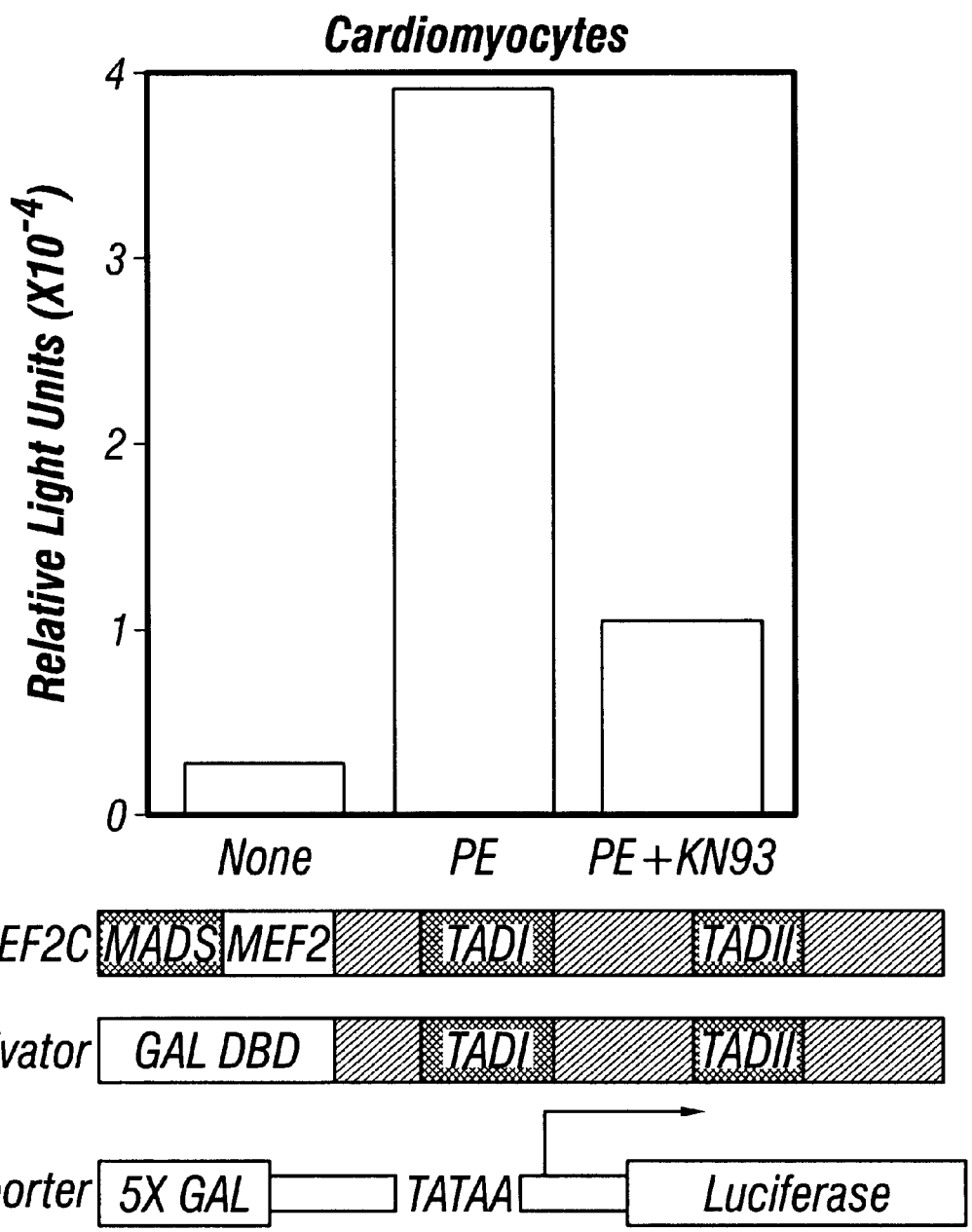
FIG. 6. Phenylephrine induces MEF2C transcriptional activity through a CaMK-dependent pathway. Cardiomyocytes were transiently transfected with expression vectors encoding GAL4-MEF2C and a GAL4-dependent reporter gene in the presence and absence of PE and the CaMK inhibitor KN-93.

In light of the ability of MEF2 to respond to calcium-dependent signal transduction pathways in T cells, the inventors have investigated whether the same pathways also activate MEF2 in cardiomyocytes. As shown in FIG. 4, activated calcineurin or CaMKIV can upregulate a MEF2-dependent luciferase reporter gene in transfected cardiomyocytes and together these calcium-sensitive signaling enzymes synergistically activate MEF2-dependent gene expression. In DNA binding assays an increase in MEF2 DNA binding activity in response to activated calcineurin and CaMKIV is not observed suggesting that the increase in MEF2 transcriptional activity reflects a post-translational mechanism. When the C-terminus of MEF2C, which contains the transcription activation domains (TADs), but lacks the MADS and MEF2 domains required for DNA binding and dimerization, is fused to the DNA binding domain of the yeast transcription factor GAL4, the resulting GAL4-MEF2C fusion protein retains sensitivity to calcineurin and CaMKIV (FIG. 5). This GAL4-MEF2C fusion protein is also activated by stimulation of cardiomyocytes with the hypertrophic agonist phenylephrine (PE) (FIG. 6). Together, these results demonstrate that the transcription activation domain of MEF2C is a nuclear target for hypertrophic signaling pathways.

Example 4

Creation of MEF2 Indicator Mice

Figure 7:
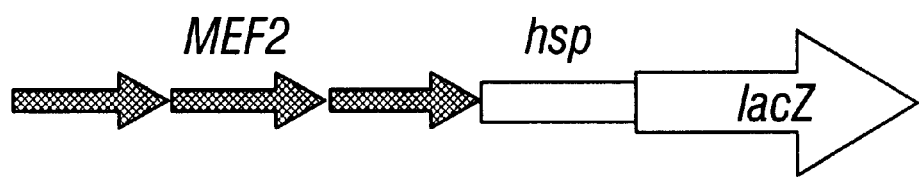
FIG. 7. Diagram of MEF2-dependent lacZ reporter gene. Three tandem copies of the MEF2 binding site from the desmin gene were cloned upstream of a lacZ reporter under control of the hsp68 promoter. This reporter was used to create transgenic mice. The sequence of the MEF2 oligonucleotide used to create the reporter is shown, with the MEF2 site underlined.

The in vitro assays support the conclusion that MEF2 is an important downstream target for hypertrophic signaling pathways in cardiomyocytes. To extend these observations to an in vivo setting, in which the time course for hypertrophic stimulation is prolonged and the physiology of an intact heart is distinct from cultured cardiomyocytes, a sensitive and specific strain of mice that faithfully reveal MEF2 activation in the heart by activation of a lacZ transgene has been developed. These mice were created using a transgene in which three tandem copies of the MEF2 site from the desmin gene were cloned upstream of the heat shock protein (hsp)-68 promoter, which is expressed at a basal level in all cells, and a lacZ reporter (FIG. 7). The sequence of the MEF2 site used to create this construct is:

GGCCTTTCCTTCTCCTCTATAAATAC-CAGCTCTGGTATTTCA

Figure 8:
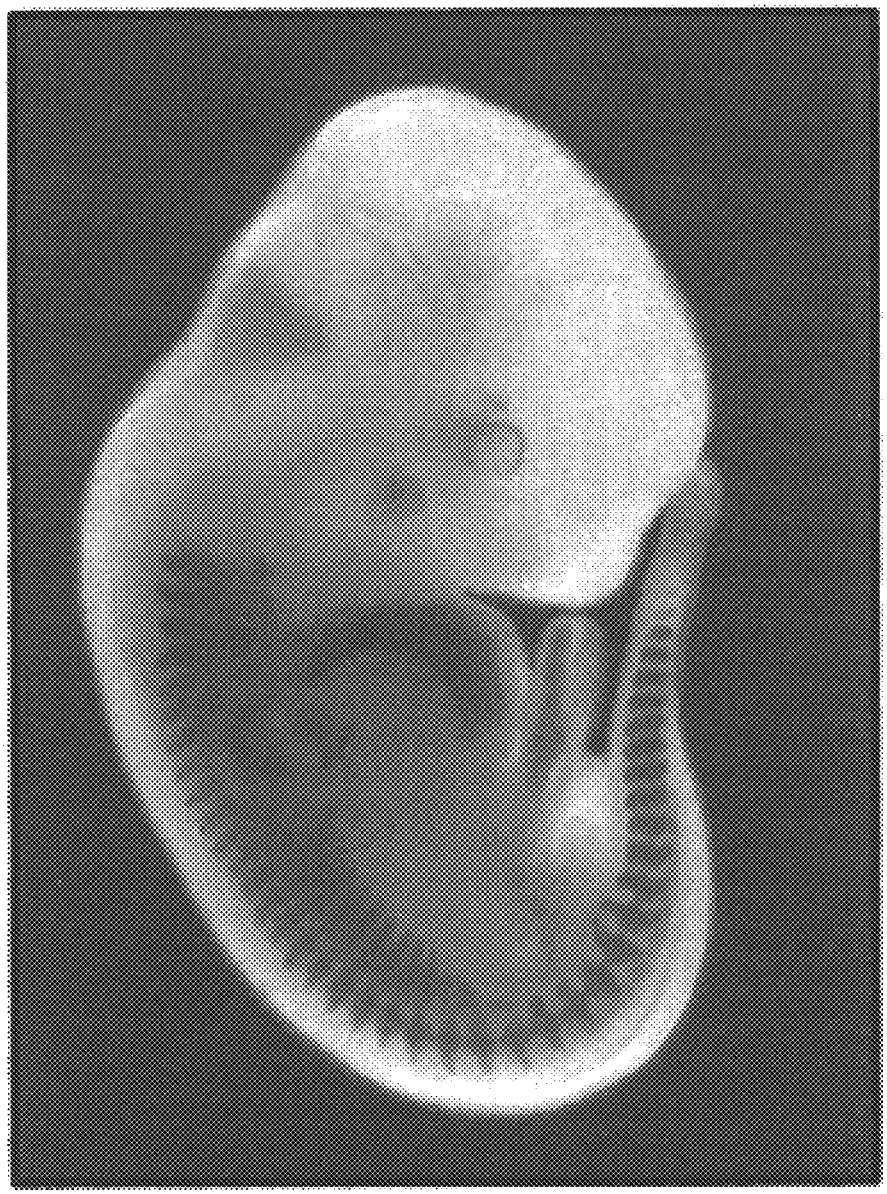
FIG. 8. LacZ staining of a transgenic mouse embryo harboring a MEF2 site-dependent lacZ transgene. The MEF2-lacZ transgene was used to generate a line of transgenic mice. A transgenic mouse embryo at E10.5 stained for lacZ expression is shown. LacZ is expressed at high levels in all developing muscle cell types; cardiac, skeletal, and smooth.
Figure 8:
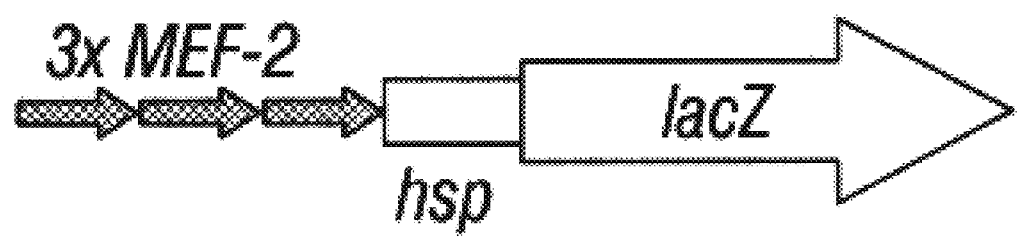

The MEF2 site is underlined in the above sequence. The inventors have characterized the expression pattern of this transgene throughout pre- and postnatal life. During embryogenesis, the MEF2 site-dependent transgene is expressed in developing muscle cell lineages (FIG. 8), consistent with the importance of MEF2 factors for activation of cardiac, skeletal, and smooth muscle gene expression. However, after birth, expression of the transgene is downregulated to levels that are undetectable by colorimetric lacZ staining of tissues.

Figure 9:
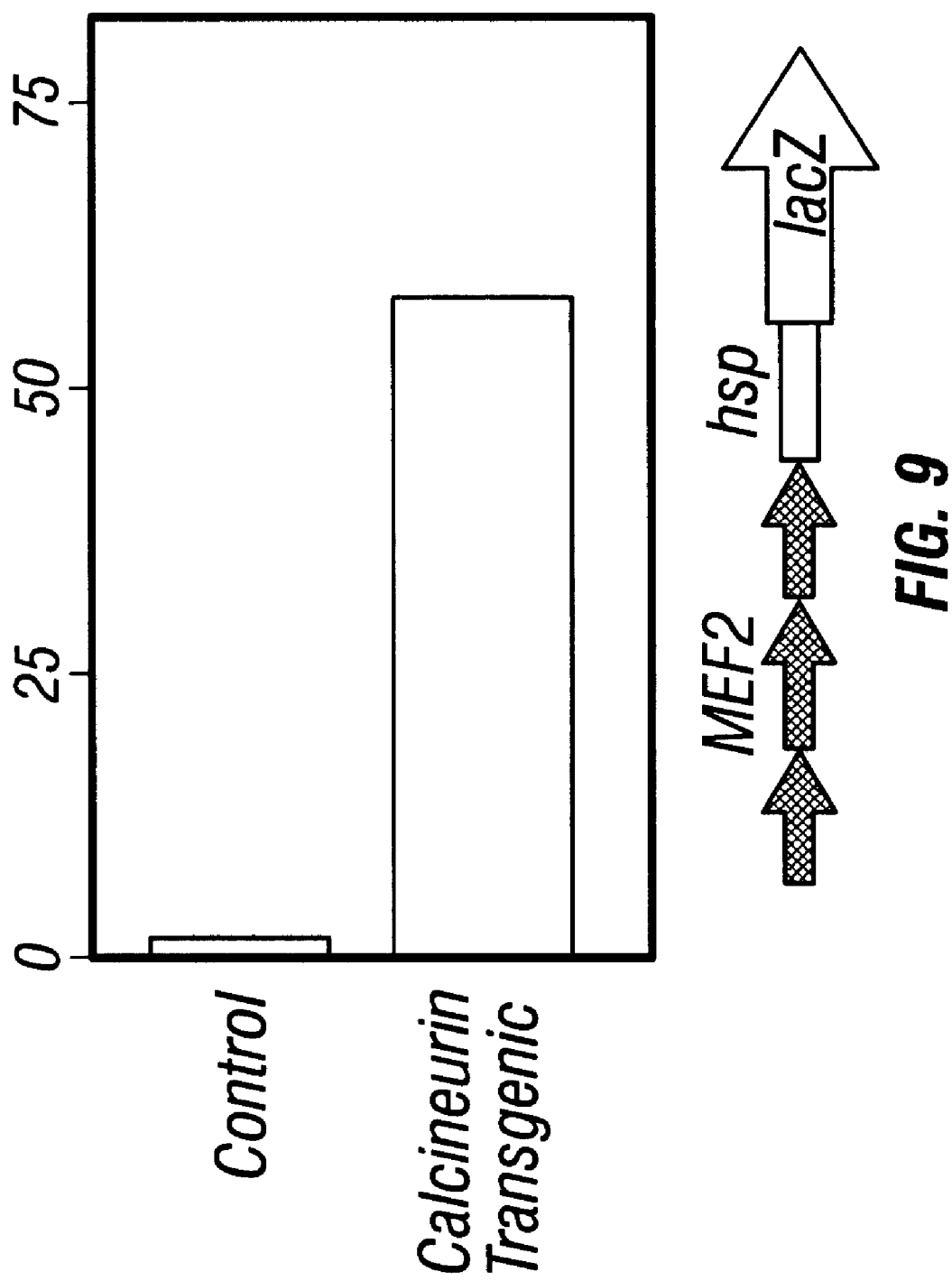
FIG. 9. Activation of MEF2-lacZ expression in the heart of a calcineurin transgenic mouse. The MEF2-lacZ transgene was introduced into a mouse strain bearing the MHC-calcineurin transgene. Mice were sacrificed at 4 weeks of age, hearts were sectioned with a vibratome, and stained for lacZ expression. LacZ is not expressed at detectable levels in littermates bearing the MEF2-lacZ transgene, but not the calcineurin transgene (control). However, lacZ expression is readily detectable throughout the MHC-calcineurin transgenic heart, which is hypertrophic.
Figure 10:
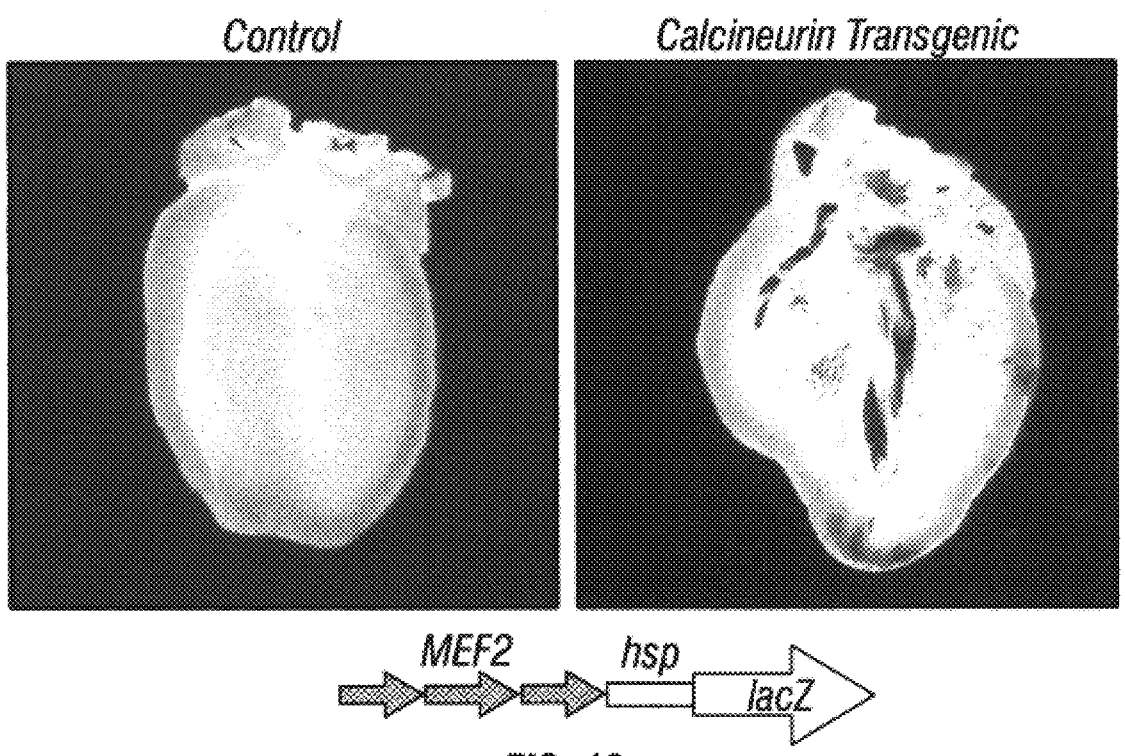
FIG. 10. Upregulation of lacZ activity from MEF2-lacZ tranisgene in the heart of a calcineurin transgenic mouse. The MEF2-lacZ transgene was introduced into a mouse strain bearing the MHC-calcineurin transgene. Mice were sacrificed at 4 weeks of age and lacZ enzyme activity was measured in heart extracts. LacZ is expressed at basal levels in hearts of littermates bearing the MEF2-lacZ transgene, but not the MHC-calcineurin transgene (control). However, lacZ expression is upregulated over 15-fold in the MHC-calcineurin transgenic heart.

To test whether the MFF2-lacZ transgene is responsive to hypertrophic signals in the heart, the inventors introduced the transgene by breeding into strains of mice bearing MHC-calcineurin and MHC-CAMKIV transgenes. As shown in FIG. 9 and FIG. 10, lacZ expression was dramatically upregulated in response to calcineurin and CAMKIV, thus mirroring activation of the hypertrophic response.

Example 5

Targeting Transcription Factors to Block Hypertrophy in Response to Multiple Signaling Pathways One of the difficulties in treating hypertrophy and heart failure by inhibiting a single signal transduction pathway is that multiple signaling systems have been shown to be activated in response to various forms of hypertrophy. Thus, inhibiting one pathway may not have a complete affect on the hypertrophic response due to other redundant pathways leading to the same endpoint. A potential means of bypassing this redundancy is to target the endpoint of the pathways where the many biochemical signaling pathways converge. Given the importance of MEF2 as a mediator of most, if not all, signaling systems leading to hypertrophy, a drug that inhibits MEF2 activity would likely by of great benefit for blunting the hypertrophic response. Moreover, the present results suggest that MEF2 is expressed at only a basal level in the adult heart, suggesting that inhibitors of MEF2 activity would be unlikely to have deleterious effects on normal cardiac function.

Example 6

Disruption of a MEF2 /Histone Deacetylase Complex by CaM Kinase Signaling in Cardiac Hypertrophy In postnatal cardiomyocytes, growth factors and other signals that activate MAPK, CaMK, and calcineurin evoke a hypertrophic response characterized by cell enlargement, activation of immediate early and fetal cardiac muscle genes, and sarcomere assembly (McKinsey and Olson, 1999). To determine whether MEF2 was a target for hypertrophic signaling in cardiomyocytes, the inventors tested whether hypertrophy in response to phenylephrine (PE) and fetal bovine serum (FBS) activated a MEF2-dependent reporter (3×MEF2-luciferase), containing three MEF2 binding sites. PE and FBS both stimulated the MEF2 reporter (FIG. 12A), but not a reporter containing a mutant MEF2 site. The amount of MEF2 DNA binding activity under these conditions was unchanged, suggesting activation of preexisting MEF2.

Figure 12B:
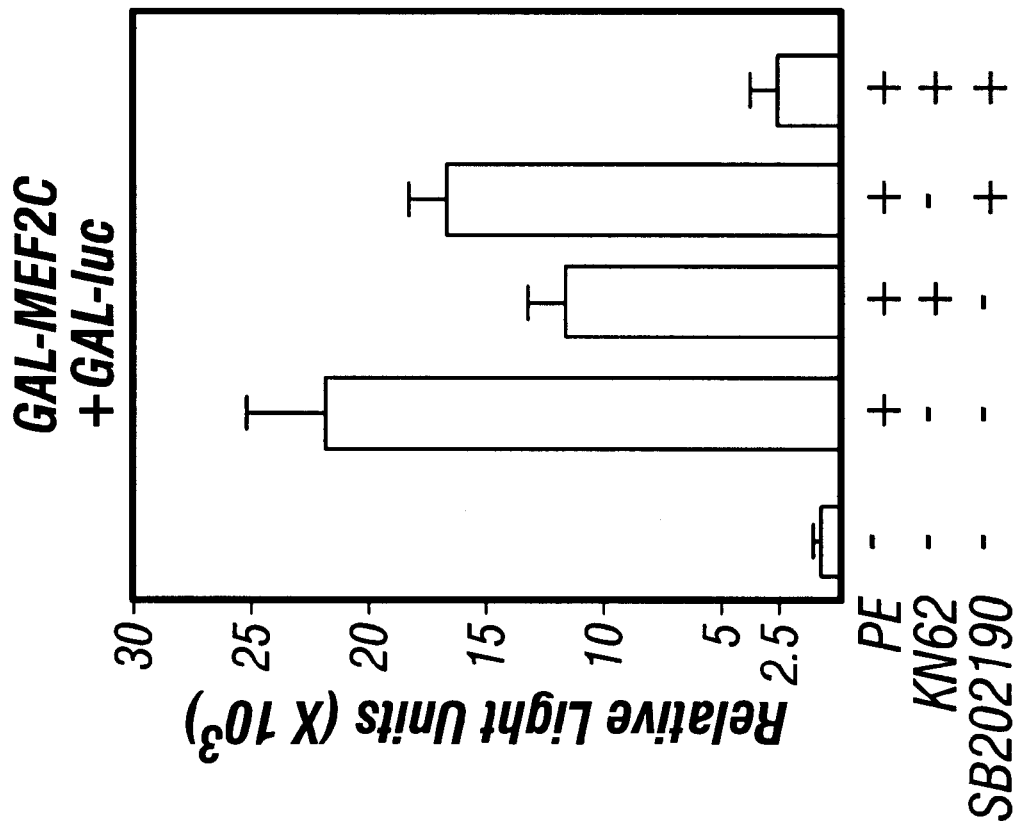
FIG. 12A, FIG. 12B and FIG. 12C. CaM kinase and MAP kinase target different domains of MEF2. Primary neonatal rat cardiomyocytes in serum-free medium were transiently transfected with the indicated expression plasmids and luciferase activity was determined in cell extracts.
Figure 12A:
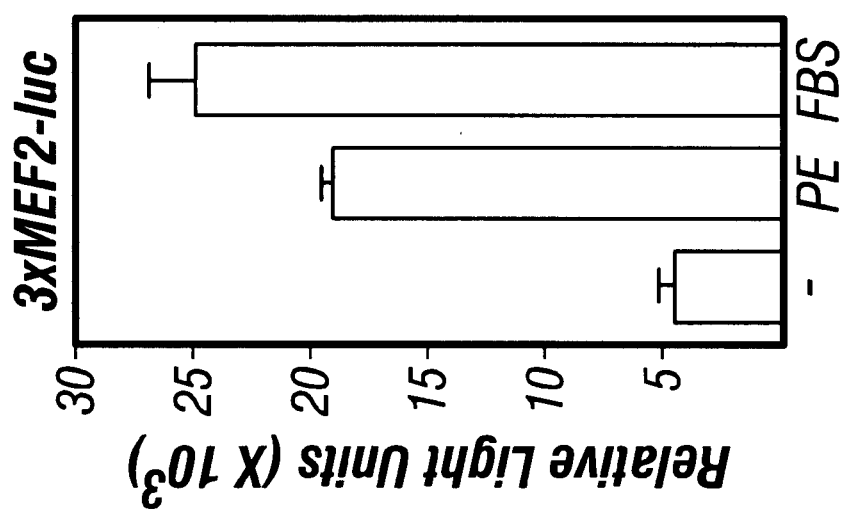

PE (FIG. 12B) and FBS also stimulated activity of a GAL4-MEF2C fusion protein, containing the complete open reading frame of MEF2C. The CaMK and p38 MAPK inhibitors, KN62 and SB202190, respectively, each partially blocked activation of GAL-MEF2C by PE, whereas both inhibitors together blocked almost all activation (FIG. 12B). This suggested that CaMK and MAPK pathways cooperated to activate MEF2 in hypertrophic cardiomyocytes.

Figure 12C:
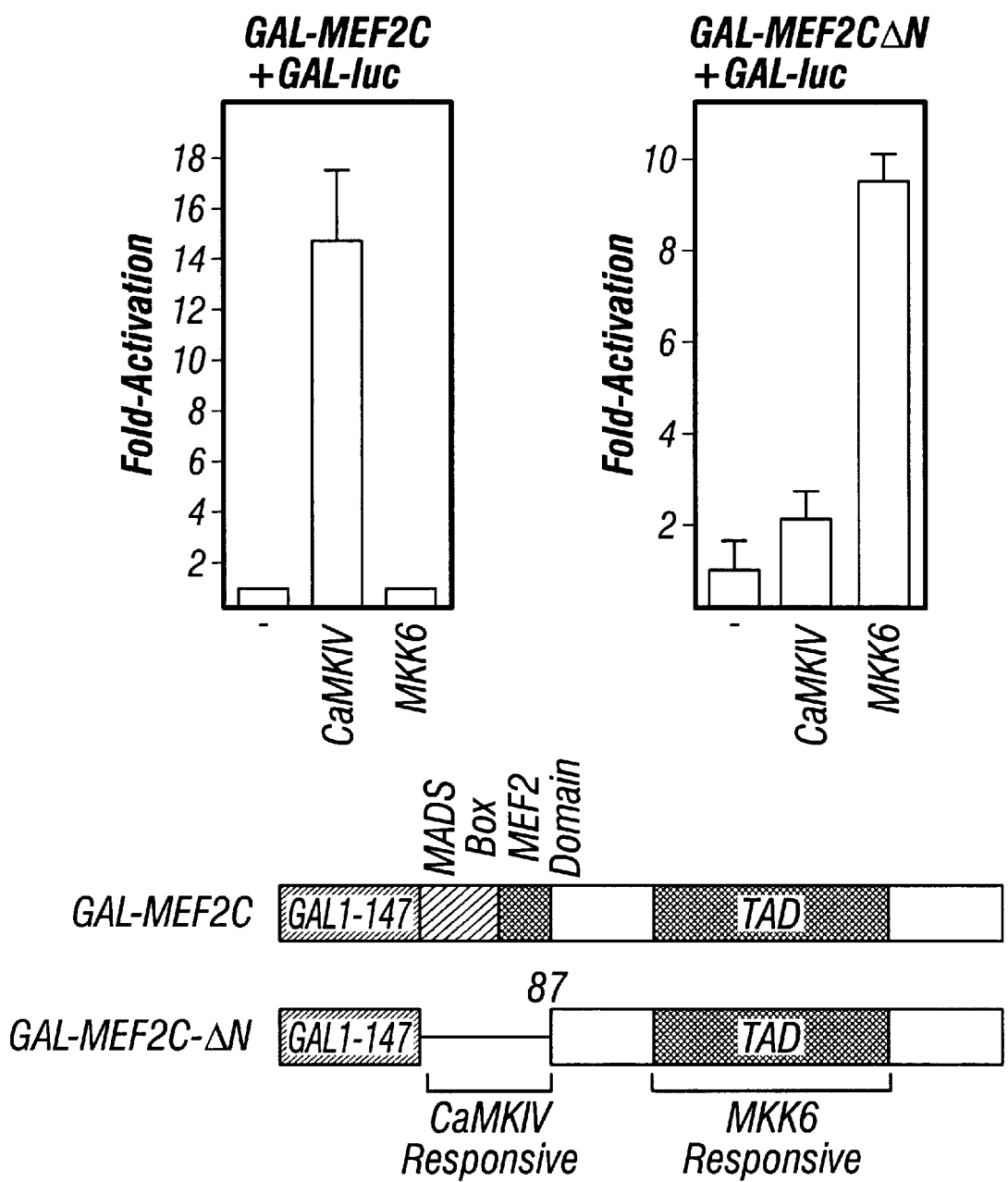

To map the regions of MEF2C that conferred responsiveness to CaMK and MAPK, the inventors compared the effects of these kinases on GAL-MEF2C and a deletion mutant containing the TAD, but lacking the MADS- and MEF2-domains (GAL-MEF2C-ΔN). Whereas activated CaMKI and CaMKIV stimulated activity of GAL-MEF2C, they had little effect on GAL-MEF2C-ΔN (FIG. 12C). In contrast, the MAPK kinase MKK6, which stimulates MEF2 by activating p38, preferentially activated GAL-MEF2C-ΔN (FIG. 12C). These results demonstrated that the CaMK and MAPK pathways targeted the N- and C-terminal regions, respectively, of MEF2C and that MADS/MEF2-region interfered with activation of the TAD by MKK6.

To determine whether cardiac hypertrophic signals also stimulated MEF2 activity in vivo, several lines of transgenic mice were created. One line expressed activated CaMKIV under control of the α-MHC promoter, which directs transgene expression specifically in the heart, resulting in cardiac hypertrophy. A second transgenic line, referred to as MEF2-indicator mice, harbored a lacZ transgene linked to three MEF2 binding sites. This reporter gene is expressed throughout the embryonic heart, consistent with the role of MEF2 in muscle development.

Figure 13A:
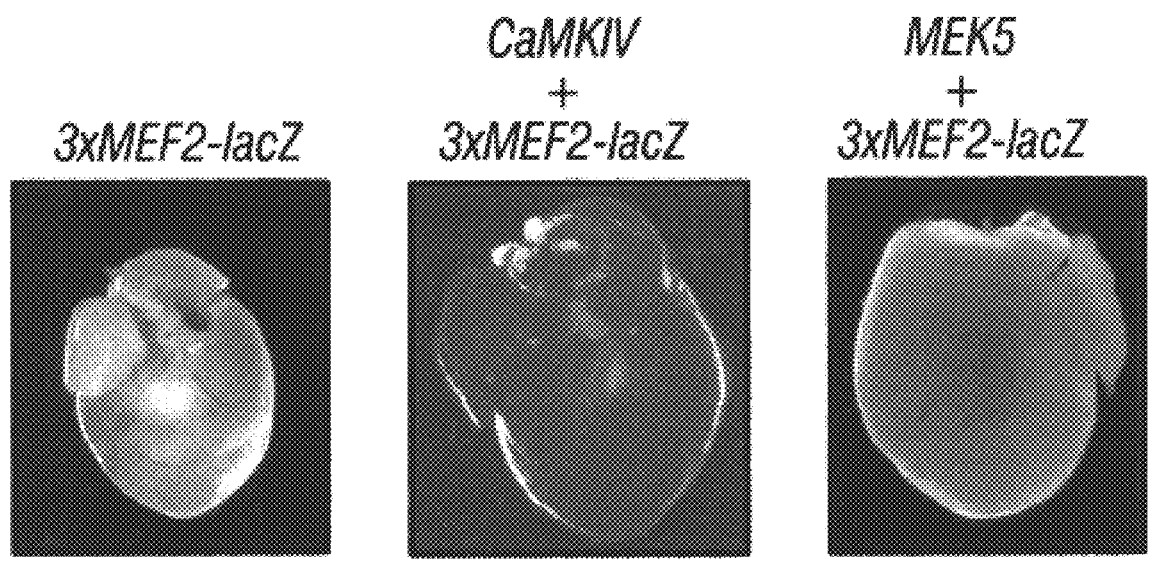
FIG. 13A and FIG. 13B. Activation of MEF2 activity by CaMKIV signaling in vivo.

Although MEF2 is expressed at high levels in the heart, the MEF2-lacZ transgene was not expressed above background levels in the heart after birth (FIG. 13A). However, the transgene was upregulated to very high levels of expression throughout the heart when it was introduced by breeding into the transgenic line bearing the (α-MHC-CaMKIV transgene (FIG. 13A). Assays on cardiac extracts showed a 145-fold increase in lacZ expression in the heart in response to CaMKIV. In contrast, cardiac expression of a transgene encoding the activated MAPK MEK5, which phosphorylates the MEF2 TAD, failed to upregulate the MEF2-lacZ reporter, in agreement with the in vitro data indicating that MAPK signaling alone in cardiomyocytes is inefficient in MEF2 activation.

Figure 13B:
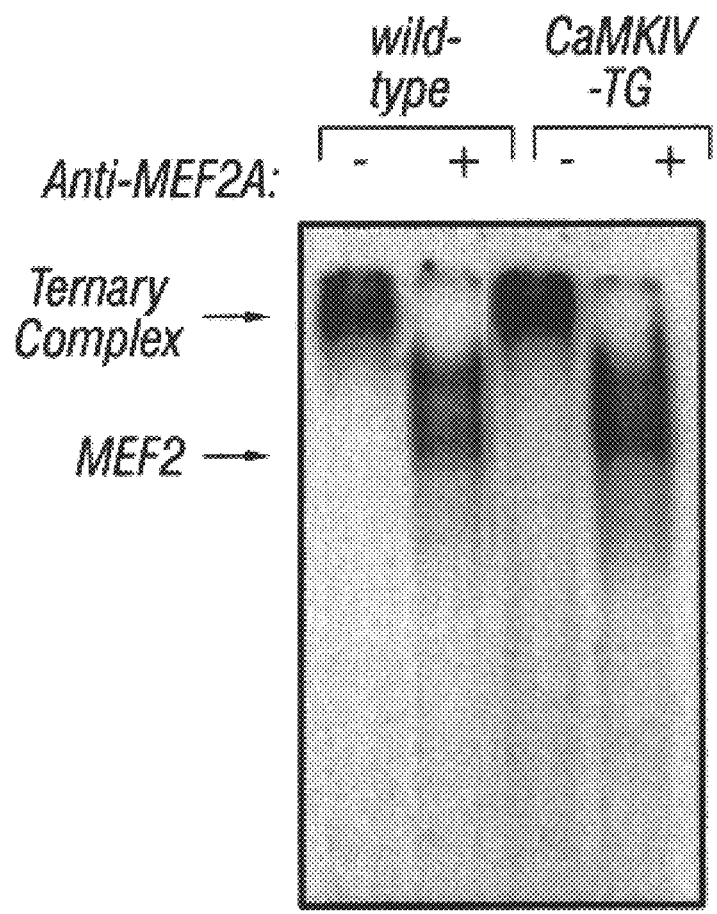

MEF2 DNA binding activity, measured by gel shift assays, was comparable in cardiac extracts from wild-type and CaMKIV transgenics (FIG. 13B). Anti-MEF2A antibody eliminated the DNA-protein complex, indicating that it was comprised of either MEF2A homo- or heterodimers (FIG. 13B).

Figure 14A:
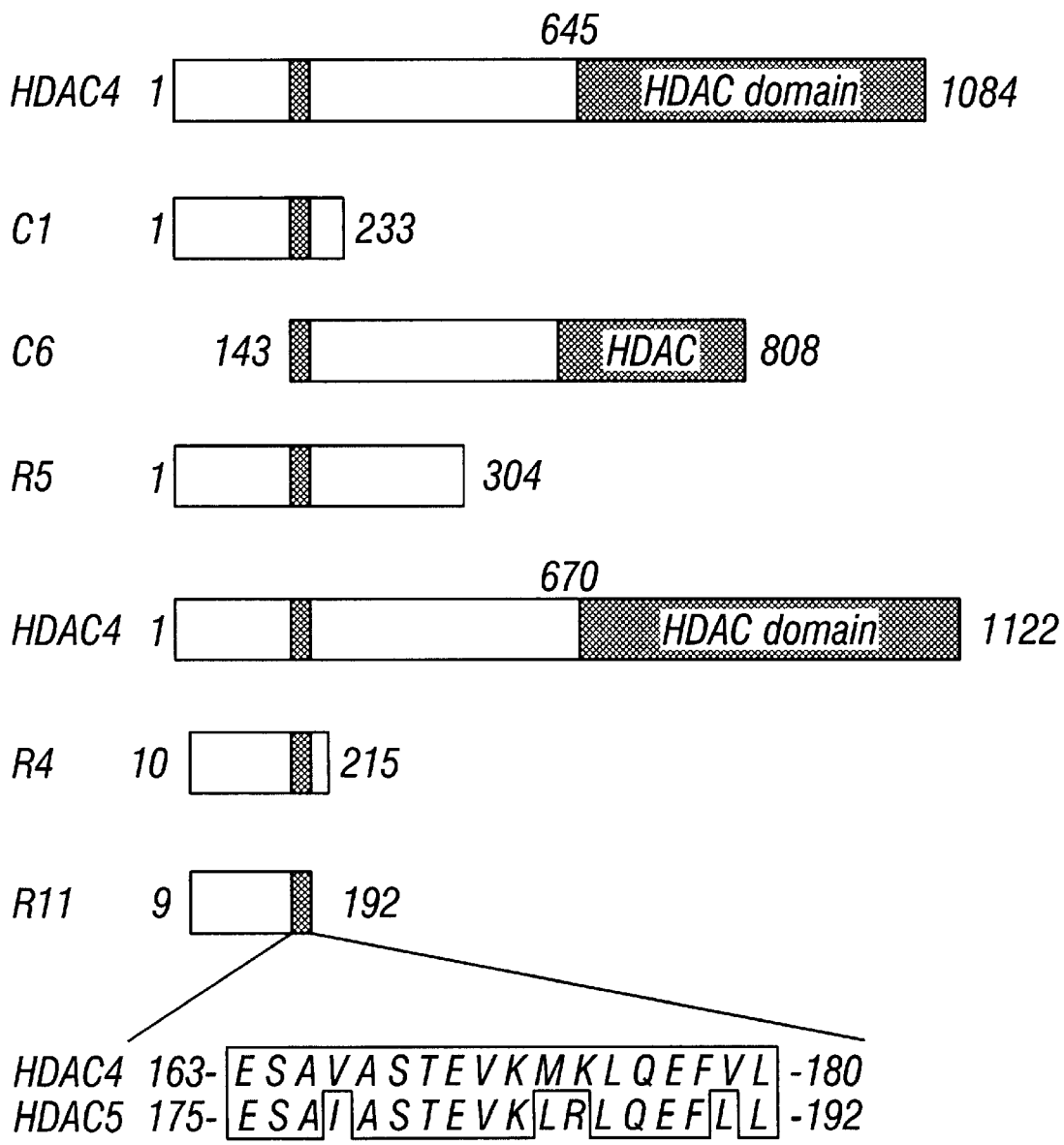
FIG. 14A, FIG. 14B, FIG. 14C and FIG. 14D. Interaction of MEF2 and HDACs 4 and 5 in yeast and mammalian cells and HDAC-mediated repression of MEF2 activity.

Because activation of MEF2 by CaMK did not affect DNA binding, the inventors performed yeast two-hybrid screens of muscle cell cDNA libraries for potential cofactors that might confer CaMK-sensitivity to MEF2. Among 11 strongly positive clones identified using the MADS-MEF2-domain (amino acids 1–86) of MEF2C fused to GAL4 as bait, nine corresponded to histone deacetylase (HDAC)-4 and two to HDAC5. MEF2 and these HDACs exhibit overlapping expression patterns, with highest expression in heart, brain, and skeletal muscle. HDACs 4 and 5 are distinguished from other HDACs by the presence of amino-terminal extensions (FIG. 14A). The portions of HDAC4 and 5 rescued from the two-hybrid screens overlapped in a nearly identical 18-amino acid segment near their amino-termini.

Figure 14B:
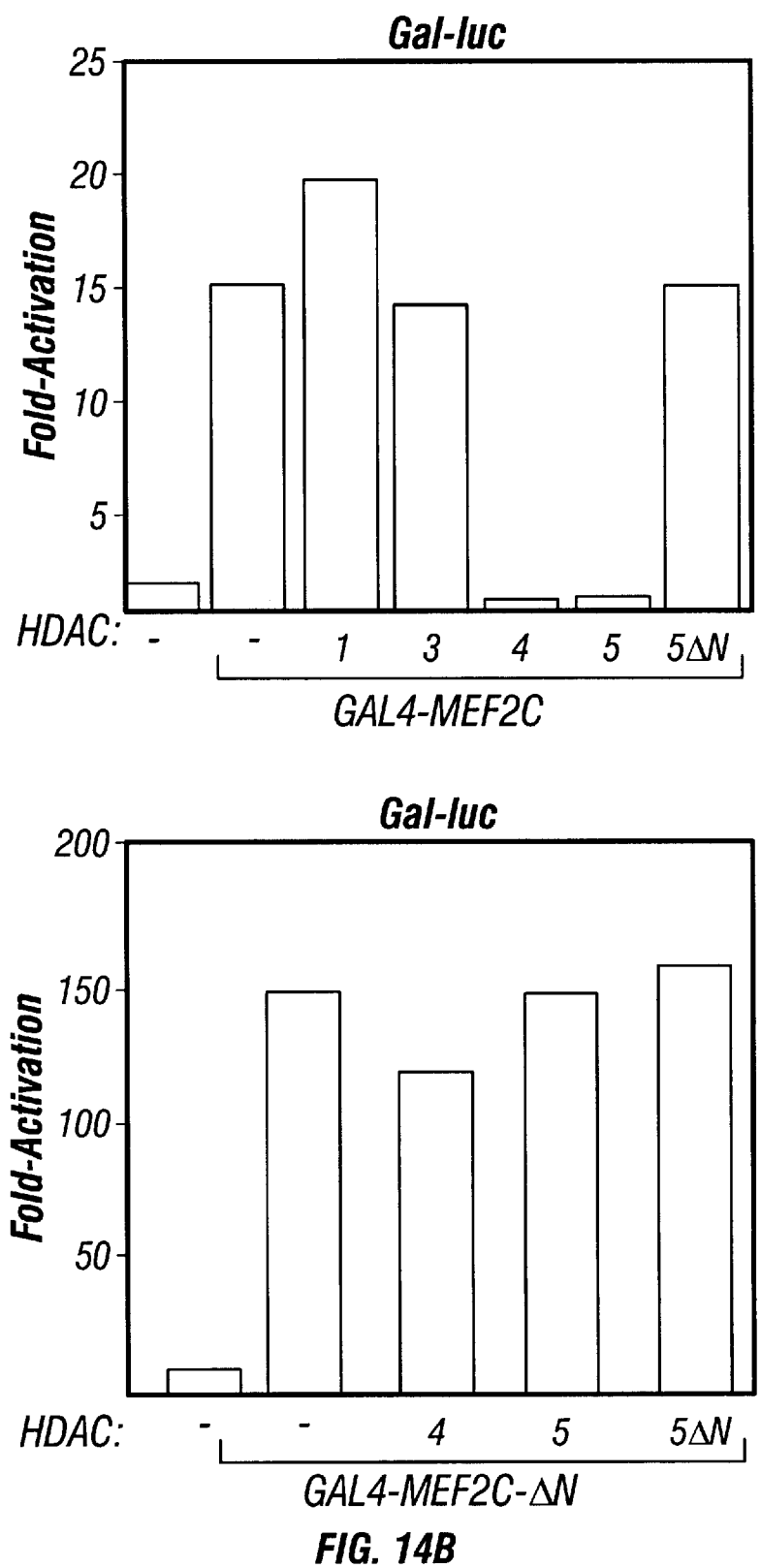

Immunoprecipitation with an antibody against a Flag-epitope tag on HDACs, followed by western blot with anti-MEF2 antibody, showed that HDACs 4 and 5 formed a complex with MEF2A, C, and D in transiently transfected 293T cells (FIG. 14B). In contrast, there was no interaction between HDACs 1 or 3 and MEF2. A HDAC5 deletion mutant lacking amino acids 22–488 (HDAC5-ΔN), including the 18-amino acid minimal MEF2-interactin region, failed to coimmunoprecipitate with MEF2 factors.

Figure 14C:
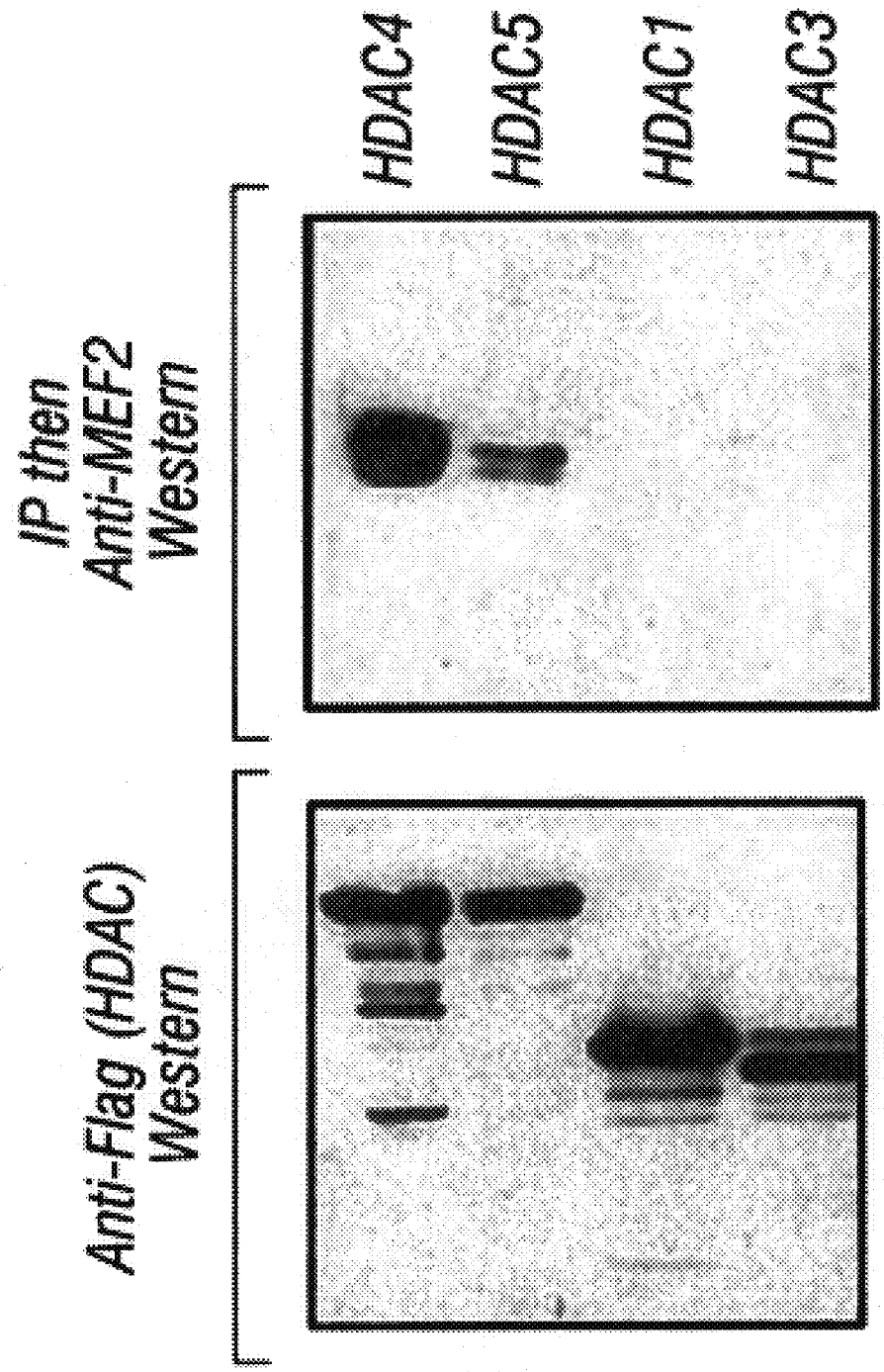

HDACs deaceylate histones when recruited to DNA, resulting in transcriptional repression. Thus, interaction of HDACs 4 and 5 with the region of MEF2 that represses the TAD suggested that this interaction played an important role in regulation of MEF2 function. In the presence of HDACs 4 and 5, MEF2A, C, and D were unable to transactivate 3×MEF2-luciferase in 10T1/2 fibroblasts, whereas in the presence of HDACs 1 or 3, these MEF2 factors were fully active. Transcriptional activity of GAL-MEF2C was also completely inhibited by HDACs 4 and 5, but not by HACs 1 or 3 or HDAC5ΔN (FIG. 14C). In contrast, GAL-MEF2C-ΔN, which lacks the HDAC-binding region, was insensitive to HDAC4 and 5 (FIG. 14C).

Figure 14D:
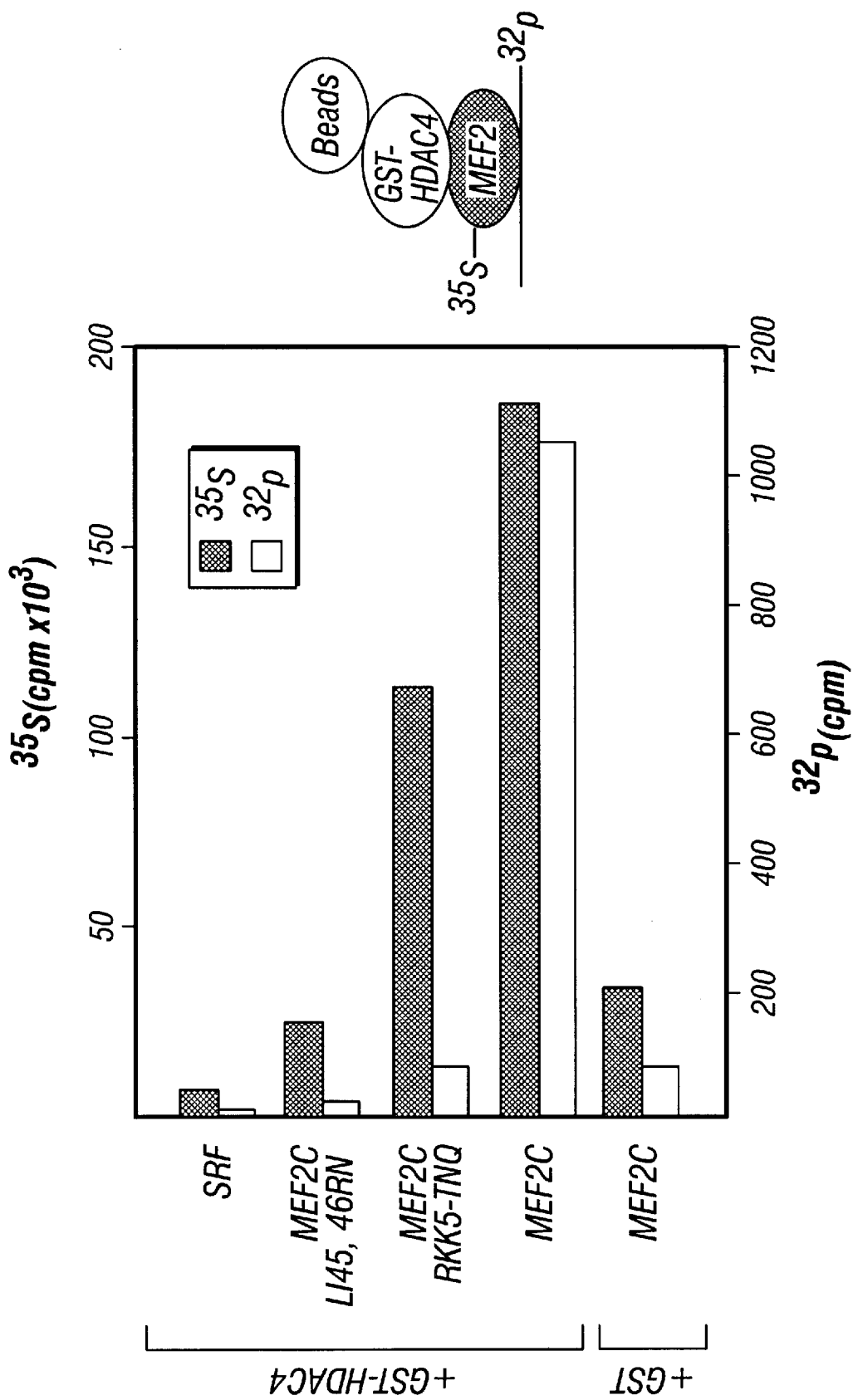

To determine whether MEF2 could bind DNA and interact with HDAC4 simultaneously, the inventors performed interaction assays with GST-HDAC4 and MEF2C translated in vitro and a labeled MEF2 binding, site. GST-HDAC4 interacted with $^{35}$S-labeled MEF2C bound to its $^{32}$P-labeled site (FIG. 14D). In contrast, there was no significant binding of MEF2C or the labeled DNA probe to GST alone. MEF2C mutant RKK3-5TNQ, binds HDAC4 in vivo but is defective in DNA binding. This mutant interacted with GST-HDAC4, but did not bring the $^{32}$P-labeled DNA binding site into the complex (FIG. 14D). The DNA binding site also was not captured by GST-HDAC4 in the presence of MEF2C mutant LI45,46RN (FIG. 14D), which was unable to interact with GST-HDAC4. Similarly, labeled SRF, which shares homology with the MADS-box of MEF2, did not associate significantly with GST-HDAC4 (FIG. 14D). Using a modified mammalian one-hybrid assay with the 3×MEF2-luciferase reporter, it also was observed that the DNA binding domain of MEF2C (amino acids 1–117) could recruit HDAC4 and 5 mutants in which the carboxyl-terminal catalytic domains were replaced with VP16, supporting the conclusion that interaction of MEF2 with HDAC4 and 5 does not interfere with binding of MEF2 to DNA. It is likely that DNA-bound MEF2 recruits HDACs to the promoter to form a ternary complex that represses transcription.

Figure 15A:
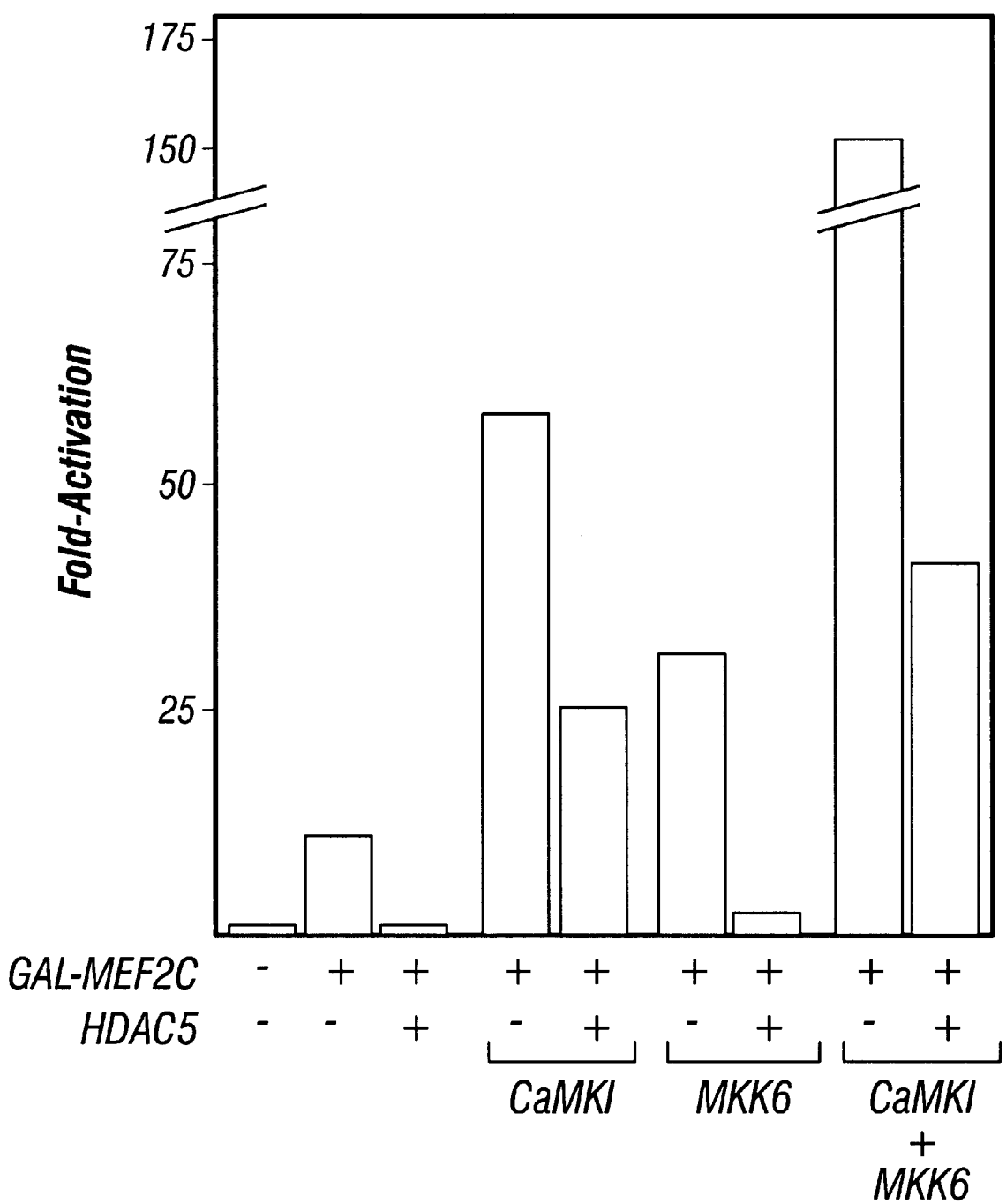

The finding that HDACs 4 and 5 interacted with the same region of MEF2 required for CaMK activation and repression of MKK6 activation suggested that signal-dependent activation of MEF2 might involve derepression by HDAC. Activated CaMKI (FIG. I5A) and CaMKIV restored transcriptional activity to GAL-MEF2C in the presence of HDAC5 (FIG. 15A). In contrast, MKK6 was unable to overcome inhibition by HDAC. MKK6 and CaMKI synergistically activated MEF2-dependent transcription.

The inventors observed no reduction in HDAC activity in cells expressing activated CaMKI or IV, suggesting that inhibition of enzyme activity was not the mechanism for CaMK-dependent activation of MEF2. It was therefore tested whether CaMK signaling might detach HDACs from MEF2. As shown in FIG. 15B activated CaMKI prevented association of HDAC5 and MEF2C or MEF2A, as detected by coimmunoprecipitation assays in transfected COS cells (FIG. 15B). In the absence of CaMKI, HDAC5 and MEF2 were both localized to the nucleus (FIG. 15C, panel a and FIG. 15C, panel b). However, in the presence of CaMKI, HDAC5 was localized to the cytoplasm, while MEF2C remained nuclear (FIG. 15C, panel c and FIG. 15C, panel d). Therefore, CaMK signaling disrupts the MEF2/HDAC complex, resulting in cytoplasmic accumulation of HDAC.

Figure 15D:
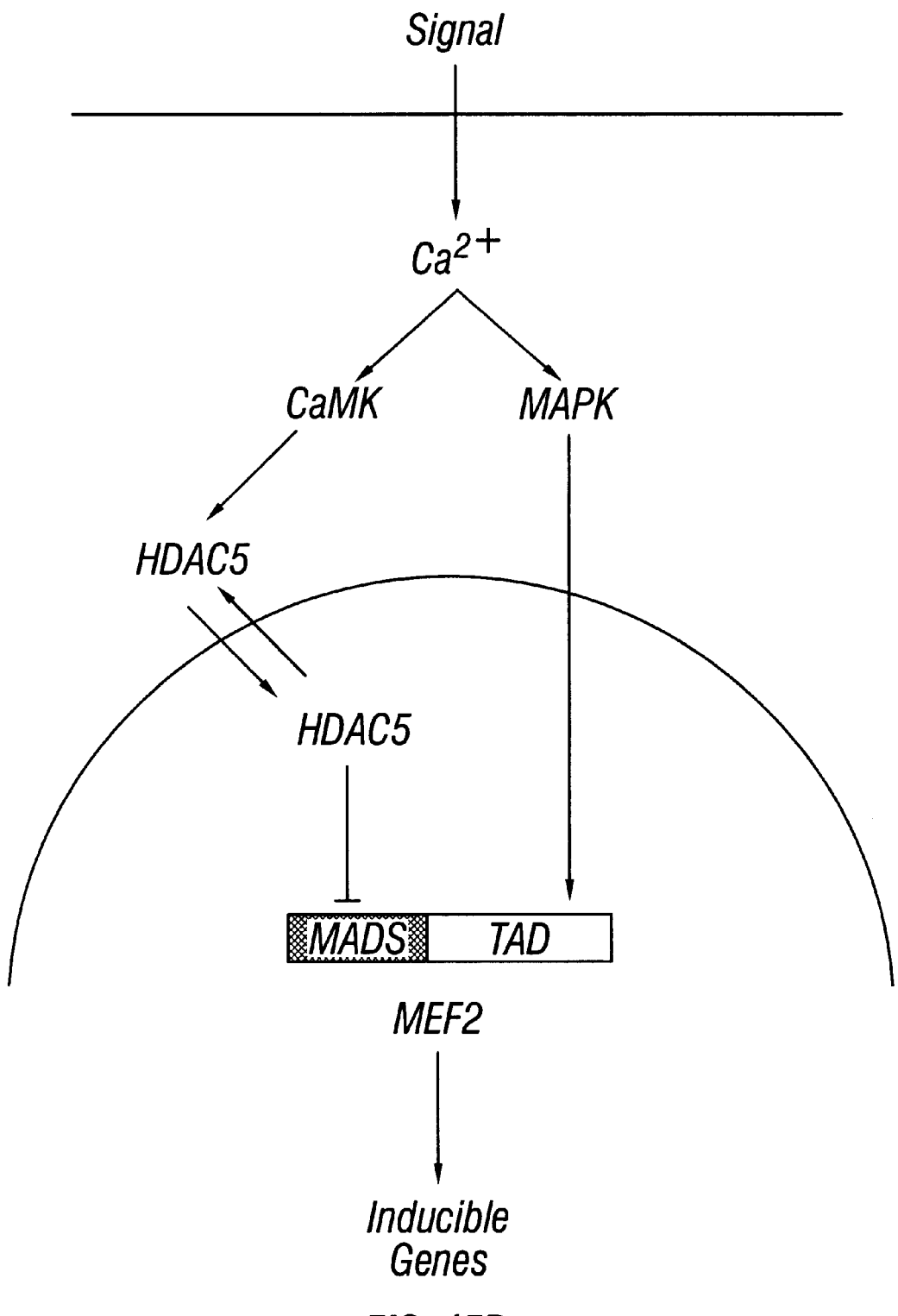
Figure 16A:
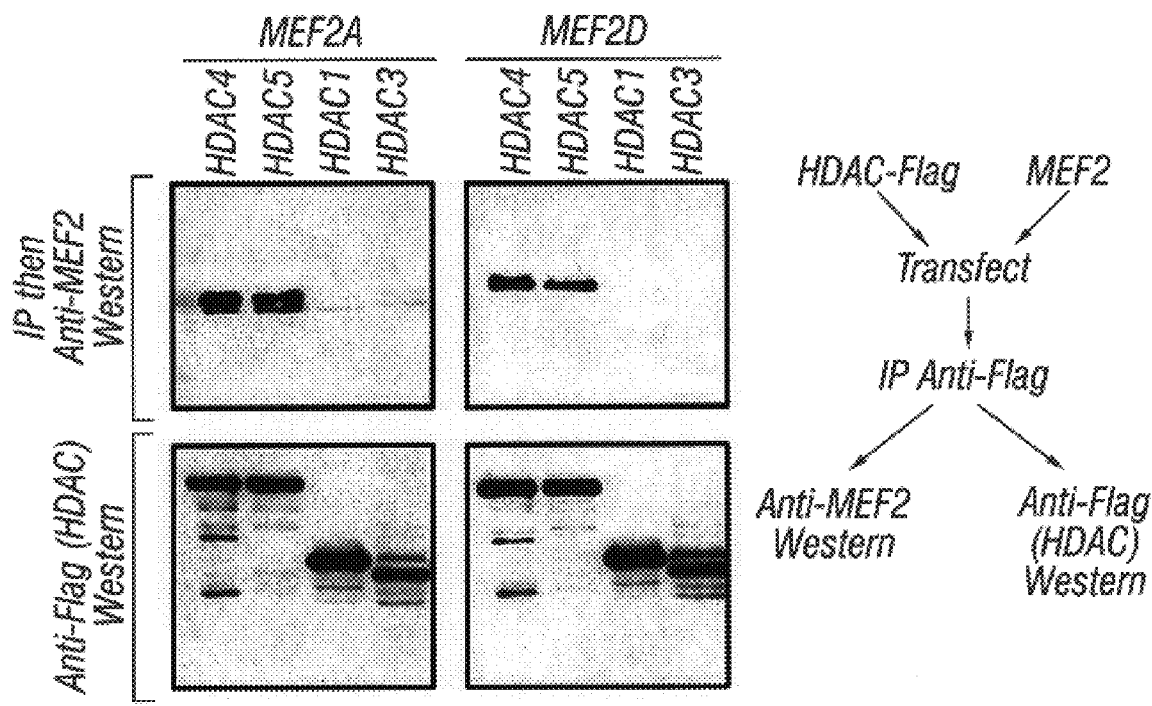
FIG. 16A and FIG. 16B. Coimmunoprecipitation of MEF2 factors and HDACs 4 and 5 from transfected cells.
Figure 16B:
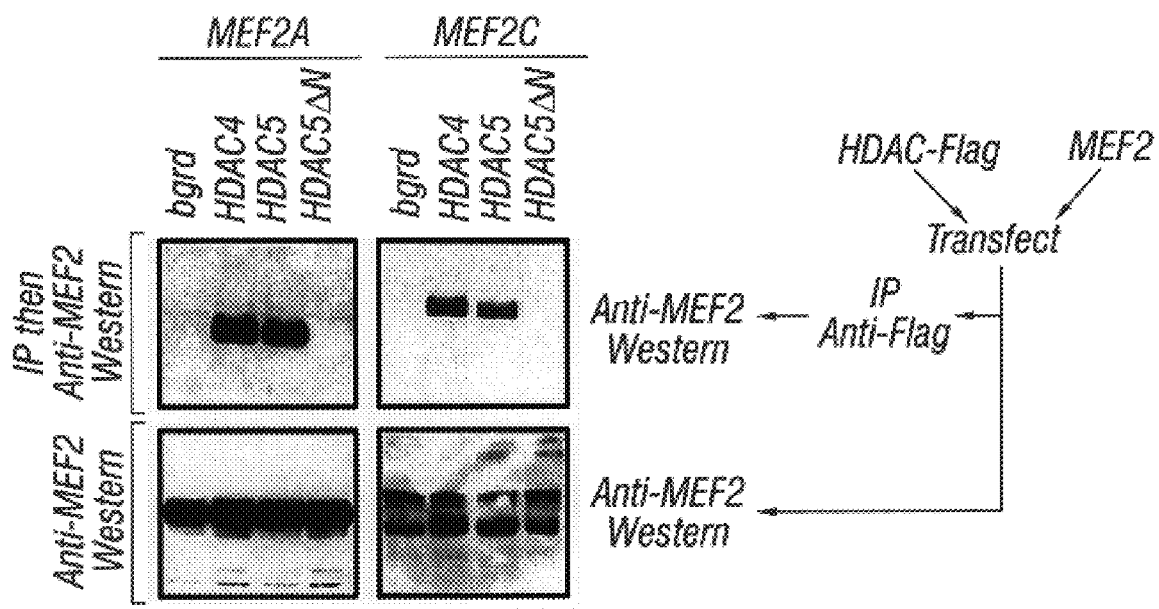
Figure 17A:
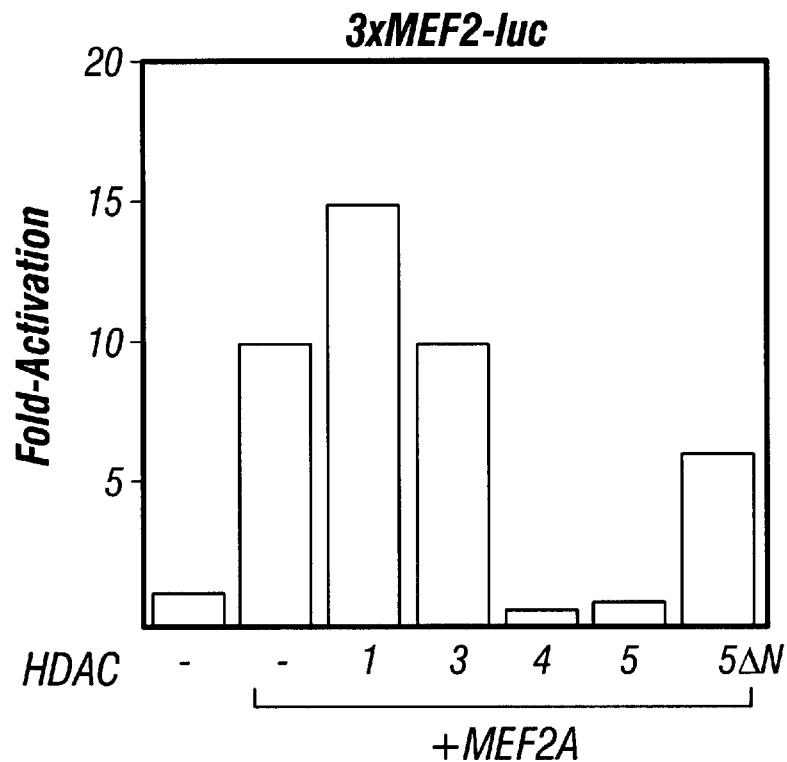
FIG. 17. Inhibition of MEF2 activity by HDACs 4 and 5. 10T1/2 cells were transiently transfected with the MEF2-dependent reporter 3×MEF2-luciferase, along with expression vectors for the indicated HDACs and MEF2 factors. Forty eight hr later, cells were harvested and luciferase activity was determined.
Figure 17B:
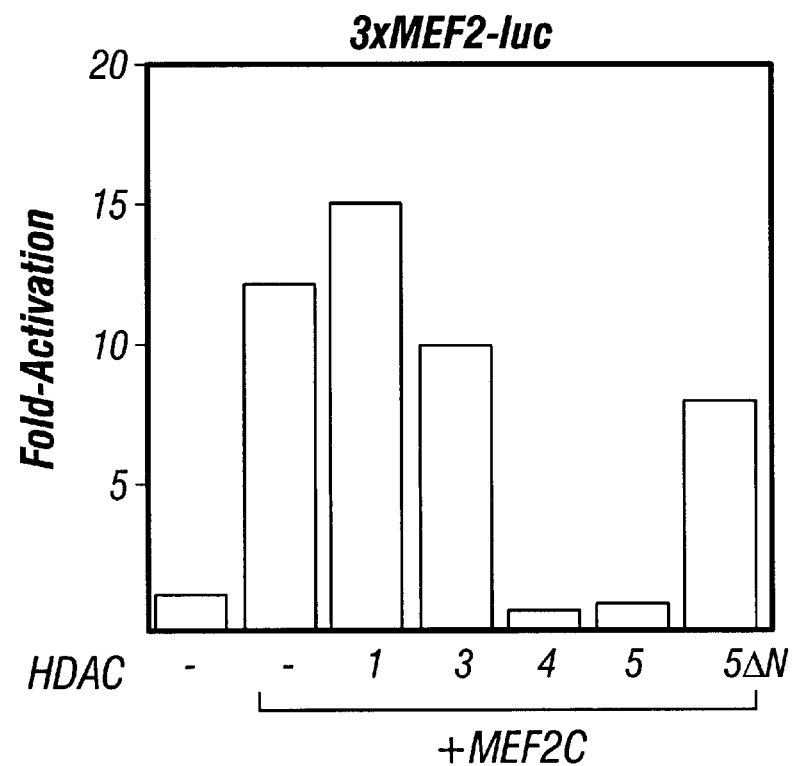
Figure 17C:
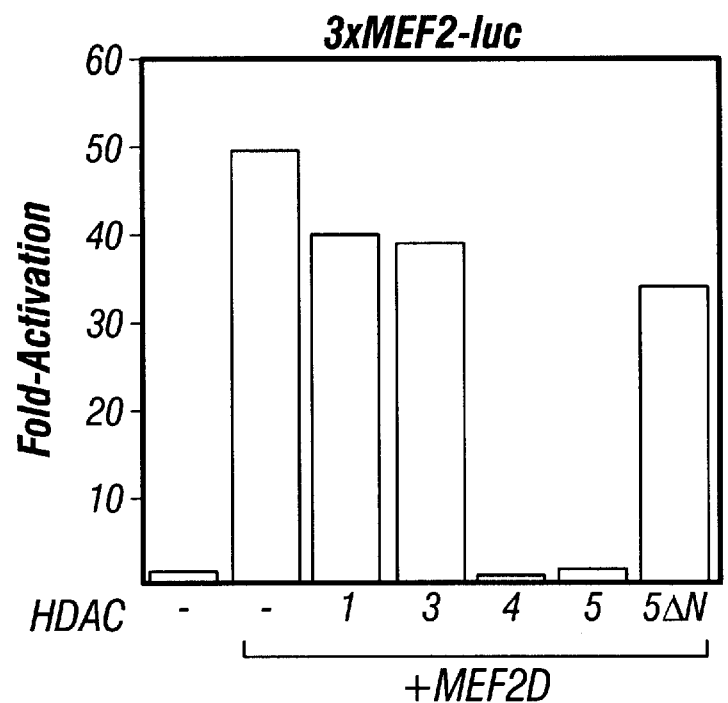
Figure 18:
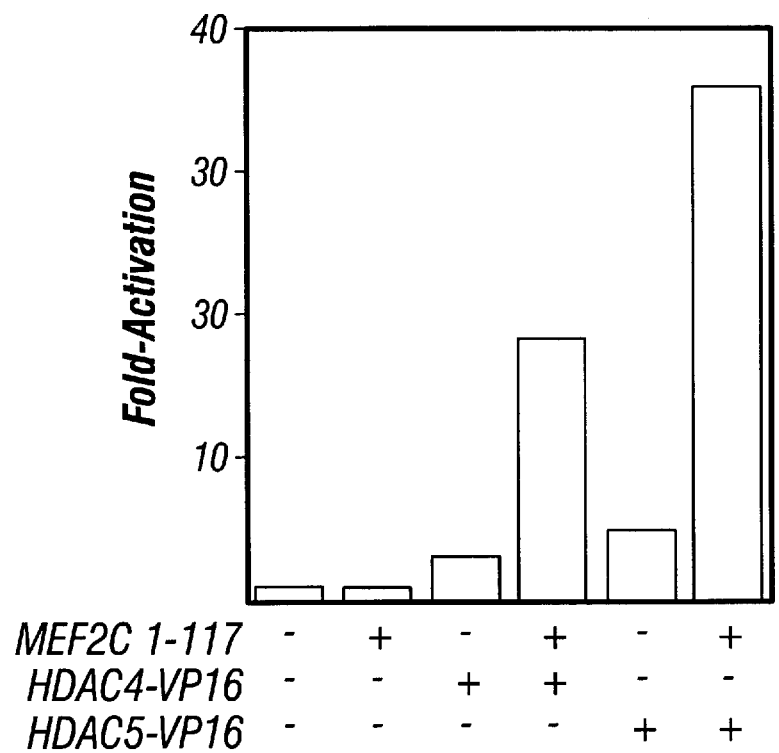
FIG. 18. Interaction of MEF2C and HDACs 4 and 5 in modified one-hybrid assay. 10T1/2 cells were transiently transfected with 3×MEF2-luciferase reporter and expression plasmids for MEF2C 1-117 and HDAC4-VP16 and HDAC5-VP16, as indicated. HDAC4-VP16 and HDAC5-VP16 were created by fusion of clones C1 and R4. respectively. VP16 in the vector pVP16 (Clontech). MEF2 1-117 was unable to activate 3×MEF2-luciferase because it lacks a TAD. However, in the presence of HDAC4-VP16 or HDAC5-VP16, MEF2 1-117 activated the reporter reflecting recruitment of these HDACs to the MEF2 binding site. In the absence of MEF2 1-117, HDAC4-VP16 and HDAC5-VP16 activated the reporter weakly, which can be attributed to interaction with endogenous MEF2D or other factors that bind the promoter.

These results demonstrate that MEF2 acts as a bipartite target for CaMK and MAPK signaling pathways (FIG. 15D), which are activated by PE in hypertrophic cardiomyocytes. CaMK signaling can unmask the transcriptional potential of MEF2 by preventing nuclear import or inducing nuclear export of HDAC5, a repressor of MEF2 activity. In contrast, activation of MEF2 by MAPK is mediated by phosphorylation of the TAD and can be prevented by association of HDAC with the DNA binding domain. Following derepression of MEF2 by CaMK signaling, coactivators with histone acetyltransferase activity, such as CBP/p300, previously shown to interact with MEF2 and to be activated by CaMKIV could be recruited to MEF2-dependent promoters, resulting in transcriptional activation.

Cardiac hypertrophy has been shown to be controlled by a signaling pathway involving calcineurin and the transcription factor NFAT3, but there is evidence for an alternate pathway. Hypertrophic activation of MEF2 by CaMK-mediated dissociation of HDAC may constitute such an alternate pathway for cardiac growth. Given the essential roles of MEF2 in muscle and neural development, HDAC and CaMK signaling also may play a role in these processes.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,359,046
U.S. Pat. No. 4,367,110
U.S. Pat. No. 4,452,901
U.S. Pat. No. 4,668,621
U.S. Pat. No. 4,873,191
U.S. Pat. No. 5,708,158
U.S. Pat. No. 5,252,479
U.S. Pat. No. 5,672,344
EPO 02/73085
WO 84/03564
Adolph, Subramaniam, Cserjesi, Olson, Robbins, "Role of myocyte-specific enhancer-binder factor (MEF-2) in transcriptional regulation of the acardiac myosin heavy chain gene," *J. Biol. Chem.*, 268:5349–5352, 1993.
Baichwal and Sugden, In: *Gene Transfer*, Kucherlapati R. ed., New York, Plenum Press, 117–148, 1986.
Batterson and Roizman, *J. Virol.*, 46:371–377, 1983.
Bedzyk et al., *J. Biol. Chem.*, 265:18615, 1990.
Bellon et al., *de Ses Filiales*, 190(1):109–142, 1996.
Benvenisty and Neshif, *Proc. Nat'l. Acad. Sci. USA*, 83:9551–9555, 1986.
Berns and Bohenzky, *Adv. Virus Res.*, 32:243–307, 1987.
Berns and Giraud, *Curr. Top. Microbiol. Immunol.*, 218:1–23, 1996.
Berns, *Microbiol Rev.*, 54:316–329, 1990.
Bertran et al., *J Virol.*, 70(10):6759–6766, 1996.
Bito, Deisseroth, Tsien, "CREB Phosphorylation and Dephosphorylation: Aca2+− and Stimulus Duration-Dependent Switch for Hippocampal Gene Expression," *Cell,*. 87:1203–1214, 1996.
Botinelli et al., *Circ. Res.* 82:106–115, 1997.
Bour, O'Brien, Lockwood, Goldstein, Bodmer, Taghert, Abmayr, Nguyen, "Drosophila MEF2, a transcription factor that is essential for myogenesis," *Genes and Dev.*, 9:730–741, 1995.
Bowman, Steinberg, Jiang, Geene, Fishman, Buttrick, "Expression of Protein Kinase C B in the Heart Causes Hypertrophy in Adult Mice and Sudden Death in Neonates," *J. Clin. Invest.*, 100:2189–2195, 1997.
Brand, "Myocyte enhancer factor 2 (MEF2)," *Int J. Biochem. Cell Biol.*, 29:1467–1470; 1997.
Brinster et al., *Proc. Nat'l. Acad. Sci. USA*, 82: 4438–4442, 1985.
Brown et al., *J. Neurochem.* 40:299–308, 1983.
Bustamante et al., *J. Cardiovasc. Pharmacol*, 17:S110–113, 1991.
Chaudhary et al., *Proc. Nat'l. Acad. Sci.*, 87:9491, 1990.
Chen and Okayama, *Mol. Cell Biol.*, 7:2745–2752, 1987.
Chien et al., *Ann. Rev. Physiol.* 55, 77–95, 1993.
Chien, Knowlton, Zhu, Chien, "Regulation of cardiac gene expression during myocardial growth and hypertrophy: Molecular studies of an adaptive physiologic response," *FASEB J.*, 5:3037–3046, 1991.
Chomczynski and Sacchi, *Anal. Biochem.*, 162:156–159, 1987.
Clarke, Arenzana, Hai, Minden, Prywe, "Epidermal Growth Factor Induction of the c-jun Promoter by a Rac Pathway," *Mol. Cell Biol.*, 18:1065–1073, 1998.
Coffin, In. Fields BN, Knipe DM, ed. Virology. New York: Raven Press, pp. 1437–1500, 1990.
Colbert, Hall, Kimball, Witt, Lorenz, Kirby, Hewett, Klevitsky, Robbins, "Cardiac Compartment-specific Overexpression of a Modified Retinoic Acid Receptor Produces Dilated Cardiomyopathy and Congestive Heart Failure in Transgenic Mice," *J. Clin. Invest.*, 100:1958–1968, 1997.
Coso, Montaner, Fromm, Lacal, Pryes, Teramoto, Gutkind, "Signaling from G Protein-coupled Receptors to the c-jun promoter Involves the MEF2 Transcription Factor," *J. Biol. Chem.*, 272:20691–20697, 1997.
Couch et al., *Am. Rev. Resp. Dis.*, 88:394–403, 1963.
DeLuca et al., *J. Virol.*, 56:558–570, 1985.
Dolmetsch, Lewis, Goodnow, Healy, "Differential activation of transcription factors induced by Ca2+ response amplitude and duration," *Nature*, 386:855–858, 1997.
Dubensky et al., *Proc. Nat'l. Acad. Sci. USA*, 81:7529–7533, 1984.
Edmondson, Lyons, Martin, Olson, "MEF2 gene expression marks the cardiac and skeletal muscle lineages during mouse embryogenesis," *Development*, 120:1251–1263, 1994.
Elroy-Stein et al., *Proc. Nat'.l Acad. Sci. USA*, 1989.
Elshami et al., *Gene Therapy*, 7(2):141–148, 1996.
Emmel, Verweij, Durand, Higgins, Lacy, Crabtree, "Cyclosporin A specifically inhibits function of nuclear proteins involved in T cell activation," *Science*, 246:1617–1620, 1989.
Evans, "Regulation of Cardiac Gene Expression by GATA-4/5/6," *Trends in Cardiovascular Medicine*, 7:75–83, 1997.
Fechheimer et al., *Proc. Nat'l. Acad. Sci. USA*, 84:8463–8467, 1987.
Feldman, Ray, Silan, Mercer, Minobe, Bristow, "Selective Gene Expression in Failing Human Heart," *Circulation*, 83:1866–1872, 1991.
Ferkol et al., *FASEB J.*, 7:1081–1091, 1993.
Flanagan, Corthesy, Bram, Crabtree, "Nuclear association of a T-cell transcription factor blocked by FK-506 and cyclosporin A," *Nature*, 352:803–807, 1991.

Fraley et al., *Proc. Nat'l. Acad. Sci. USA,* 76:3348–3352, 1979.
French et al., *Circulation,* 90(5):2414–2424, 1994.
Freshner, In *Animal Cell Culture: a Practical Approach* Second Edition. Oxford/New York, IRL Press, Oxford University Press, 1992.
Ghosh and Bachhawat, (Wu G, Wu C ed.), New York: Marcel Dekker, pp. 87–104, 1991.
Ghosh-Choudhury et al., *EMBO J.,* 6:1733–1739, 1987.
Ginsberg et al., *Proc. Nat'l. Acad. of Sci. USA,* 88(5) 1651–1655, 1991.
Glorioso et al., *Ann. Rev. Microbiol.* 49:675–710, 1995.
Gomez-Foix et al.,*J. Biol. Chem.,* 267:25129–25134, 1992.
Gopal, *Mol. Cell Biol.,* 5:1188–1190, 1985.
Gossen and Bujard, "Tight control of gene expression in mammalian cells by tetracycline-responsive promoters," *Proc. Nat'l. Acad. Sci.,* 89:5547–5551, 1992.
Gossen et al., *Science,* 268:1766–1769, 1995.
Graham and Prevec, *Biotechnology,* 20:363–390, 1992.
Graham and Prevec, In: E. J. Murray (ed.), Methods in Molecular Biology: Gene Transfer and Expression Protocol, Clifton, N.J.: Humana Press, 7:109–128, 1991.
Graham and Van Der Eb, *Virology,* 52:456–467, 1973.
Graham et al., *J. Gen. Virol.,* 36:59–72, 1977.
Grepin et al., *Mol. Cell. Biol.,* 14:3115–3129, 1994.
Grunhaus and Horwitz, *Seminar in Virology,* 3:237–252, 1992.
Gruver, DeMayo, Goldstein, Means, "Targeted developmental overexpression of calmodulin induces proliferative and hypertrophic growth of cardiomyocytes in transgenic mice," *Endocrinology,* 133:376–388, 1993.
Han, Jiang, Li, Kravchenko, Ulevitch, "Activation of the transcription factor MEF2C by the MAP kinase p38 in inflammation," *Nature,* 386:296–299, 1997.
Harland and Weintraub,*J. Cell Biol.,* 101:1094–1099, 1985.
Harlow et al., *Antibodies: A Laboratory Manual,* Cold Spring Harbor, N.Y., 1988.
Hasegawa, Lee, Jobe, Markham, Kitsis, "Cis-acting sequences that mediate induction of the -myosin heavy chain gene expression during left ventricular hypertrophy due to aortic constriction," *Circulation,* 96:3943–3953, 1997.
Haverich et al., *Transplant Proc.,* 26:2713–2715, 1994.
Hersdorffer et al., *DNA Cell Biol.,* 9:713–723, 1990.
Herz and Gerard, *Proc. Nat'l. Acad. Sci. USA,* 90:2812–2816, 1993.
Herzig, Jobe, Aoki, Molkentin, Cowley, Izumo, Markham, "Angiotensin II type 1a receptor gene expression in the heart: AP-1 and GATA-4 mediate the response to pressure overload," *Proc. Nat'l. Acad. Sci. USA,* 94:7543–7548, 1997.
Ho et al., *J. Biol. Chem.,* 270:19898–19907, 1995.
Ho, Gullberg, Chatila, "Activation of protein I-dependent transcriptional activation of interleukin 2 gene by $Ca^{++}$/calmodulin kinase type IV/Gr," *J. Exp. Med.,* 184:101–112, 1996.
Hoey, Sun, Williamson, Xu, "Isolation of two new members of the NF-AT gene family and functional characterization of the NF-AT proteins," *Immunity,* 2:461–472, 1995.
Hogan et al., *"Manipulating the Mouse Embryo"* Cold Spring, Harbor Laboratory, Cold Spring Harbor, N.Y., 1986.
Holland et al., *J. Virology,* 101:10–18, 1980.
Honess and Roizman,*J. Virol.,* 14:8–19, 1974.
Honess and Roizman,*J. Virol.,* 16:1308–1326, 1975.
Hongo et al., *Am. J. Physiol.,* 269:C690–C697, 1995.
James and Olson, "Deletion of the regulatory domain of protein kinase C exposes regions in the hinge and catalytic domains that mediate nuclear targetinog," *J. Cell Biol.,* 116:863–874, 1992.
Johnson et al., *BIOTECHNOLOGY AND PHARMACY,* Pezzuto et al., eds., Chapman and Hall, New York, 1993.
Jones and Shenk, *Cell,* 13:181–188, 1978.
Jones et al., *J. Clin. Invest.,* 98:1906–1917, 1996.
Jones, Sanchez, Robbins, "Murine pulmonary myocardium: developmental analysis of cardiac gene expression," *Dev. Dyn.,* 200:117–128, 1994.
Kaneda el al., *Science,* 243:375–378, 1989.
Kariya, Karns, Simpson, "An enhancer core element mediates stimulation of the rat-myosin heavy chain promoter by an $_1$-adrenergic agonist and activated -protein kinas C in hypertrophy of cardiac myocytes," *J. Biol. Chem.,* 269:3775–3782, 1994.
Karliner, Kariya, Simpson, "Effects of pertussis toxin on 1-agonist-mediated phosphatidylinositide turnover anh myocardial cell hypertrophy in neonatal rat myocytes," *Experientia.,* 46:81–84, 1990.
Karlsson et al., *EMBO J.,* 5:2377–2385, 1986.
Karns, Kariya, Simpson, "M-CAT, CarG. and Sp1 elements are required for $_1$-adrenergic induction of the skeletal -actin promoter during cardiac myocyte hypertrophy," *J. Biol. Chem.,* 270:410–417, 1995.
Kato et al., *J. Biol. Chem.,* 266:3361–3364, 1991.
Kato, Kravchenko, Tapping, Han, Ulevitch, Lee, "BMK1/ERK5 regulates serum-induced early gene expression through, transcription factor MEF2C," *EMBO J.,* 16:054–066, 1997.
Kearns et al., *Gene Ther.,* 3:748–755, 1996.
Kincaid, Giri, Higuchi, Tamura, Dixon, Marietta, Amorese, Martin, "Cloning and characterization of molecular isoforms of the catalytic subunit of calcineurin using nonisotopic methods," *J. Biol. Chem.,* 265:11312–11319, 1990.
Klein et al., *Nature,* 327:70–73, 1987.
Komuro and Yazaky, "Control of cardiac gene expression of mechanical stress," *Annu. Rev. Physiol.,* 55:55–75, 1993.
Kotin and Berns, *Virol.,* 170:460–467, 1989.
Kotin et al., *Genomics,* 10:831–834, 1991.
Kotin et al., *Proc. Nat'l. Acad. Sci. USA,* 87:2211–2215, 1990.
Kovacic-Milivojevic, Wong, Gardner, "Selective regulation of the atrial natriuretic peptide gene by individual components of the activator protein-1 complex," *Endocrinology,* 137:1008–1117, 1996.
Kudoh et al., *Circ. Res.,* 80:139–146, 1997.
LaPointe et al., *Hypertension,* 27:715–722, 1996.
Le Gal La Salle et al., *Science,* 259:988–990, 1993.
Le Guennec et al., *Exp. Physiol.,* 6:975–978, 1991.
Lee, Nadal-Ginard, Mahdavi, Izumo, "Myocyte-Specific Enhancer Factor 2 and Thyroid Hormone Receptor Associate and Synergistically Activate the α-Cardiac Myosin Heavy-Chain Gene," *Mol. Cell Biol.,* 17:2745–2755, 1997.
Leite, Page, Ambler, "Regulation of ANP secretion by endothelin-1 in cultured atrial myocytes: desensitization and receptor subtype," *Am. J. Physiol.,* 267:H2193–2203, 1994.
Levrero et al., *Gene, 101:195–202, 1991.*
Li, Zhou, James, Heller-Harrison, Czech, Olson., "FGF inactivates myogenic helix- loop-helix proteins through phosphorylation of a conserved protein kinase C site in their DNA binding domains," *Cell,* 71:1181–1194, 1992.
Lilly, Zhao, Ranganayakulu, Paterson, Schulz, Olson, "Requirement of MADS domain transcription factor D-MEF2 for muscle formation in Drosophila," *Science,* 267:688–693, 1995.

Lin et al., *J. Clin. Invest.*, 97:2842–2848, 1996.

Lin, Schwarz, Olson, "Control of cardiac morphogenesis and myogenesis by the myogenic transcription factor MEF2C," *Science*, 276:1404–1407, 1997.

Liu, Liu, Borras, Chatila, Speck, "Cyclosporin A-sensitive induction of the Epstein-Barr virus lytic switch is mediated via a novel pathway involving a MEF2 family member," *EMBO J.*, 16:143–153, 1997.

Loh et al., *J. Biol. Chem.*, 271:10884–10891, 1996b.

Loh et al., *Mol. Cell. Biol.*, 16:3945–3954, 1996a.

Lyakh el al., *Mol. Cell. Biol.*, 17:2475–2482, 1997.

Mann et al., *Cell*, 33:153–159, 1983.

Marban et al., *Proc. Nat'l. Acad. Sci. USA*, 84:6005–6009, 1987.

Markowitz et al., *J. Virol.*, 62:1120–1124, 1988.

Martin, Schwarz, Olson, "Myocyte enhancer factor (MEF) 2C: A tissue-restricted member of the MEF-2 family of transcription factors," *Proc. Nat'l. Acad. Sci. USA*, 90:5282–5286, 1993.

Masuda, Naito, Tokumitsu, Campbell, Saito, Hannum, Arai, Arai, "NF-ATx, a novel member of the nuclear factor of activated T cells family that is expressed predominately in the thymus," *Mol. Cell Biol.* 15:2697–2706, 1995.

McCaffery et al., *Science*, 262:750–754, 1993.

McKinsey and Olson, *Curr. Opin. In Genetics & Dev.* 9, 267, 1999.

Mercadier, Lompre, Due, Boheler, Fraysse, Wisnewsky, Allen, Komajda, Schwartz, "Altered sarcoplasmic reticulum $Ca^{++}$-ATPase gene expression in the human ventricle during end-stage heart failure," *J. Clin. Invest.*, 85:305–309, 1995.

Mizukami et al., *Virology*, 217:124–130, 1996.

Molkentin and Olson, "Combinational Control of Muscle Development by bHLH and MADS-box Transcription Factors," *Proc. Nat'l. Acad. Sci. USA*, 93:9366–9373, 1996.

Molkentin and Olson, *Circulation*, 96:3833–3835, 1997.

Molkentin et al., *Mol. Cell. Biol.*, 14:4947–4957, 1994.

Molkentin, Black, Martin, Olson, "Cooperative activation of muscle gene expression by MEF2 and myogenic bHLH proteins," *Cell*, 83:1125–1136, 1995.

Molkentin, Black, Martin, Olson, "Mutationial analysis of the DNA binding, dimerization, and transcriptional activation of MEF2C," *Mol. Cell. Biol.*, 16:2627–2636, 1996a.

Molkentin, Firulli, Black, Lyons, Edmondson, Hustad, Copeland, Jenkins, Olson, "MLF2B is a potent transactivator expressed in early myogenic lineages," *Mol. Cell. Biol.*, 16:3814–3824, 1996b.

Molkentin, Li, Olson, "Phosphorylation of the MADS-box transcription factor MEF2C enhances its DNA binding activity," *J. Biol. Chem.*, 271:17199–17204, 1996c.

Molkentin, Lin, Olson, "Requirement of the GATA4 Transcription factor for heart tube formation and ventral morphogenesis," *Genes and Dev.*, 11:1061–1072, 1997.

Morgan et al., *Annu. Rev. Physiol.*, 49:533–543, 1987.

Mulligan, *Science*, 260:926–932, 1993.

Myers, EPO 0273085.

Nicolas and Rubenstein, In: *Vectors: A survey of molecular cloning vectors and their uses.* Rodriguez and Denhardt (eds.), Stoneham: Butterworth, pp. 494–513, 1988.

Nicolau and Sene, *Biochem. Biophys. Acta*, 721:185–190, 1982.

Nicolau et al., *Methods Enzymol.*, 149:157–176, 1987.

Northrop et al., i Nature, 369:497–502, 1994.

Northrop, Ho, Chen, Thomas, Timmerman, Nolan, Admon, Crabtree, "NF-AT components define a family of transcription factors targeted in T-cell activation," *Nature*, 369:497–502, 1994.

Ogawa et al., *J. Mol. Med.*, 73:457–463, 1995.

Ogawa, *Neuropathologica*, 77(3):244–253, 1989.

O'Keefe, Tamura, Kincaid, Tocci, O'Neill, "FK506- and CsA-senisitive activation of the interleukin-2 promoter by calcineurin," *Nature*, 357:692–694, 1992.

Olson, Perry, Schulz, "Regulation of muscle differentiation by the MEF2 family of MADS box transcription factors," *Developmental Biology*, 172:2–14, 1995.

Ostrove et al., *Virology*, 113:532–533, 1981.

Palmiter and Solaro, *Basic. Res. Cardial.*, 92:63–74, 1997.

Palmiter et al., *Nature*, 300:611, 1982.

Paradis, MacLellan, Belaguli, Schwartz, Schneider, "Serum response factor mediates AP-1 dependent induction of the skeletal α-actin promoter in ventricular myocytes" *J. Biol. Chem.*, 271:10827–10833, 1996.

Park, Takeuchi, Sharma, "Characterization of a new isoform of the NF-AT (nuclear family of activated T cells) gene family member NF-ATc," *J. Biol. Chem.*, 271:20914–20921, 1996.

Paskind et al., *Virology*, 67:242–248, 1975.

Perales et al., *Proc. Nat'l. Acad. Sci.*, 91:4086–4090, 1994.

Perreault et al., *Am. J. Physiol.*, 266:H2436–H2442, 1994.

Ponnazhagan et al., *Hum. Gene Ther.*, 8:275–284, 1997a.

Ponnazhagan et al., *J. Gen. Virol.*, 77:1111–1122, 1996.

Post et al., *Cell*, 24:555–565, 1981.

Potter et al., *Proc. Nat'l Acad. Sci. USA*, 81:7161–7165, 1984.

Racher et al., *Biotechnology Techniques*, 9:169–174, 1995.

Radler et al., *Science*, 275:810–814, 1997.

Ragot et al., *Nature*, 361:647–650, 1993.

Ramirez, Zhao, Schulman, Brown, "The Nuclear ob isoform of Ca2+/Calmodulin-dependent Protein Kinase Ii Regulates Atrial Natriuretic Factor Gene Expression in Ventricular Myocytes," *J. Biol. Chem.*, 272:31203–31208, 1997.

Rao, Luo, Hogan, "Transcription factors of the NF-AT family: Regulation and function," *Ann. Rev. Immunol.*, 15:707–747, 1997.

Reid and Yacoub, "Determinants of left ventricular function one year after cardiac transplantation," *Br. Heart J.*, 59:397–402, 1988.

Renan, Radiother, Oncol., 19:197–218, 1990.

Rich et al., Hum. Gene Ther., 4:461–476, 1993.

Ridgeway, In: Vectors: A survey of molecular cloning vectors and their uses. Eds. Rodriguez R L and Denhardt D T, pp. 467–492, 1988.

Rippe et al., Mol. Cell Biol., 10:689–695, 1990.

Roizmani and Sears, In Fields' Virology, 3rd Edition, eds. Fields et al. (Raven Press, New York, N.Y.). pp. 2231–2295, 1995.

Rooney, Hodge, McCaffrey, Rao, Glimcher, "A common factor regulates both Th1- and The-specific cytokine gene expression," *EMBO J.*, 13:625–633, 1994.

Rosenfeld et al., Cell, 68:143–155, 1992.

Rosenfeld et al., Science, 252:431–434, 1991.

Roux et al., Proc. Nat'l Acad. Sci. USA, 86:9079–9083, 1989.

Sadoshima and Izumo, "Signal transduction pathways of angiotensin II-induced c-fos gene expression in cardiac myocytes in vitro," *Circ. Res.*, 73:424–438, 1993b.

Sadoshima and Izumo, "The cellular and molecular response of cardiac myocytes to mechanical stress," *Ann. Rev. Physiol.*, 59:551–571, 1997.

Sadoshima, Xu, Slayter, Izumo, "Autocrine release of angiotensin II mediates stretch-inducedhypertrophy of cardiac myocytes in vitro," *Cell*, 75:977–984. 1993a.

Saeki et al., Adv. Exp. Med. Biol., 332:639–647, 1993.

Sambrook et al., Molecular Cloning: A Laboratory Manual Cold Spring Harbor Laboratory, Cold Spring Harbor, N.Y., 1989.

Samulski et al., EMBO J., 10:3941–3950, 1991.

Schwartz et al., Circ. Res. 59:551–555, 1986.

Schwinger, Bohm, Schmidt, Karczewski, Bevendick, Flesch, Krause, Erdmann, "Unchanged protein levels of SERCA II and phospholamban but reduced $Ca^{2+}$-ATPase activity of cardiac sarcoplasmic reticulum from dilated cardiomyopathy patients compared with patients with nonfailing hearts," Circulation, 92:3220–3228, 1995.

Shiraishi et al., Transplant International, 1-0(3):202–206, 1997.

Smith and Moss, Gene, 25:21–28, 1983.

Song et al., Science, 275:536–540, 1997.

Srivastava et al., J. Virol., 45:555–564, 1983.

Stemmer and Klee, "Dual calcium ion regulation of calcineurin by calmodulin and calcineurin B," Biochemistry, 33:6859–6866, 1994.

Stratford-Perricaudet and Perricaudet, In: Human Gene Transfer, Eds. O. Cohen-Haguenauer and M. Boiron, Editions John Libbey Eurotext, France, pp. 51–61, 1991.

Su, Zhao, Weber, Eugster, Ryffel, "Distribution and activity of calcineurill in rat tissues. Evidence for post-transcriptional regulation of testis-specific calcineurin B," Eur. J. Biochem., 230:469–474, 1995.

Tate-Ostroff et al., Proc. Nat'l. Acad. Sci., 86:745–749, 1989.

Temin, In: Gene Transfer, Kucherlapati (ed.), New York: Plenum Press, pp. 149–188, 1986.

Terzic, Puceat, Vassort, Vogel, "Cardiac α-1 adrenoceptors: an overview," Pharm. Rev., 45:147–175, 1993.

The Qiagenologist, Application Protocols, 3rd edition, published by Qiagen, Inc., Chatsworth, Calif.

Thorburn, Thorburn, Chen, Powers, Shubeita, Feramisco, Chein, "HRas dependent pathways can activate morphological and genetic markers of cardiac muscle cell hypertrophy," J. Biol. Chem., 268:2344–2349, 1993.

Theurauf and Glembotski, J. Biol. Chem., 272:7464–7472, 1997.

Thuerauf and Glembotski, "Differential effects of protein kinase C, Ras, and Raf-1 kinase on the induction of the cardiac B-type natriuretic peptide gene through a critical promoter-proximal M-CAT element," J. Biol. Chem., 272:7464–7472, 1997.

Top et al., J. Infect. Dis., 124:155–160, 1971.

Tur-Kaspa et al., Mol. Cell Biol., 6:716–718, 1986.

Varmus et al., Cell 25:23–36, 1981.

Vikstrom and Leinwand, Curr. Opin. Cell Biol., 8:97–105, 1996.

Wagner et al., Proc. Nat'l. Acad. Sci., 87(9):3410–3414, 1990.

Watkins et al., Hum. Mol. Genet., 4:1721–1727, 1995.

Werthman et al., Journal of Urology, 155(2):753–756, 1996.

Wolfe, Zhou, Dotsch, Chen, You, Ho, Crabtree, Wagner, Verdine, "Unusual Rel-like architecture in the DNA-binding domain of the transcription factor NFATc," Nature, 385:172–176, 1997.

Wong et al., Gene, 10:87–94, 1980.

Woods and Ellis, In: Laboratory Histopathology: A Complete Reference. p 7.1–13. Churchill Livingstone Publishers, New York, 1994.

Woronicz, Lina, Calnan, Szychowski, Cheng, Winoto, "Regulation of the Nur77 Orphan Steroid Receptor in Activation-Induced Apoptosis," Mol. Cell. Biol. 6364–6376, 1995.

Wu & Wu. Biochemistry, 27:887–892, 1988.

Wu & Wu, J. Biol. Chem., 262:4429–4432, 1987.

Wu and Wu, Adv. Drug Delivery Rev., 12:159–167, 1993.

Yamazaki et al., Circulation, 95:1260–1268, 1997.

Yamazaki et al., J. Biol. Chem., 271:3221–3228, 1996.

Yang et al., Proc. Nat'l. Acad. Sci USA, 87:9568–9572, 1990.

Yu, Redfern, Fishman, "Conditional transgene expression in the heart," Circ. Res., 75:691–697, 1996.

Zou et al., J. Biol. Chem., 271:33592–33597, 1996.

Zou, Komuro, Yamazaki, Aikawa, Kudoh, Shiojima, Hiro, Mizuno, Yasaki, "Protein Kinasc C, but not tyrosine Kinases or Ras, Plays a Critical Role in angiotensin II-induced Activation of Raf-1 Kinase and Extracellular Signal-related Protein Kinases in Cardiac Myocytes," J. Biol. Chem., 271:33592–33597, 1996.

What is claimed is:

1. A transgenic mouse, whose genome comprises an indicator gene under the control of a transcriptional regulatory element, wherein said transcriptional regulatory element comprises a MEF2 binding site and said indicator gene is (a) expressed in embryonic cardiac tissue, (b) not expressed in adult cardiac tissue, and (c) expressed in adult cardiac tissue in response to hypertrophic signals.

2. A method of screening for modulators of MEF2-induced gene expression comprising the steps of:
   (a) providing a cell whose genome comprises an indicator gene under the control of a transcriptional regulatory element comprising a MEF2 binding site, wherein said indicator gene is (a) expressed in embryonic cardiac tissue, (b) not expressed in adult cardiac tissue, and (c) expressed in adult cardiac tissue in response to hypertrophic signals;
   (b) contacting said cell with a candidate modulator; and
   (c) monitoring said cell for expression of said indicator gene as compared to a cell not treated with said candidate modulator,
wherein said contacting is performed in vivo in the transgenic mouse of claim 1.

3. A method of screening for modulators of MEF2-induced gene expression comprising the steps of:
   (a) providing a cell whose genome comprises an indicator gene under the control of a transcriptional regulatory element comprising a MEF2 binding site, wherein said indicator gene is (a) expressed in embryonic cardiac tissues (b) not expressed in adult cardiac tissue, and (c) expressed in adult cardiac tissue in response to hypertrophic signals;
   (b) contacting said cell with a candidate modulator; and
   (c) monitoring said cell for expression of said indicator gene as compared to a cell not treated with said candidate modulator,
wherein said cell is from the transgenic mouse of claim 1.

4. The transgenic mouse of claim 1, wherein said transcriptional regulatory element comprises two MEF2 binding sites.

5. The transgenic mouse of claim 1, wherein said transcriptional regulatory element comprises three MEF2 binding sites.

6. The transgenic mouse of claim 1, wherein said indicator gene is selected from the group consisting of lacZ, a gene encoding green fluorescent protein and a gene encoding luciferase.

7. A method of screening for modulators of MEF2-induced gene expression comprising the steps of:
   (a) providing a cell whose genome comprises an indicator gene under the control of a transcriptional regulatory element comprising a MEF2 binding site, wherein said indicator gene is (a) expressed in embryonic cardiac tissue, (b) not expressed in adult cardiac tissue, and (c) expressed in adult cardiac tissue in response to hypertrophic signals;

(b) contacting said cell with a candidate modulator; and (c) monitoring said cell for expression of said indicator gene as compared to a cell not treated with said candidate modulator.

8. The method of claim 7, wherein said cell is from a cardiomyocyte line.

9. The method of claim 7, wherein said cell is from a primary cardiomyocyte.

10. The method of claim 7, wherein contacting is performed in vitro.

11. The method of claim 7, wherein said candidate modulator is an antisense construct.

12. The method of claim 7, wherein said candidate modulator is from a small molecule library.

13. The method of claim 7, wherein said candidate modulator is an antibody.

14. The method of claim 13, wherein said antibody is a single chain antibody.

15. The method of claim 7, wherein said transcriptional regulatory element comprises two MEF2 binding sites.

16. The method of claim 7, wherein said transcriptional regulatory element comprise three MEF2 binding sites.

17. The method of claim 7, wherein said indicator gene is selected from the group consisting, of lacZ, a gene encoding green fluorescent protein and a gene encoding luciferase.

* * * * *

UNITED STATES PATENT AND TRADEMARK OFFICE
CERTIFICATE OF CORRECTION

PATENT NO. : 6,372,957 B1
DATED : April 16, 2002
INVENTOR(S) : Eric N. Olson

It is certified that error appears in the above-identified patent and that said Letters Patent is hereby corrected as shown below:

<u>Title page,</u>
Item [54], please insert -- A -- before "TRANSGENIC" therefor.
Item [57], ABSTRACT,
Line 5, please delete "hypertroplic" and insert -- hypertrophic -- therefor.

<u>Column 54,</u>
Line 11, please delete "comprise" and insert -- comprises -- therefor.
Line 14, please delete "consisting," and insert -- consisting -- therefor.

Signed and Sealed this

Twenty-fourth Day of September, 2002

*Attest:*

*Attesting Officer*

JAMES E. ROGAN
*Director of the United States Patent and Trademark Office*